(12) United States Patent
Steichen et al.

(10) Patent No.: US 7,231,290 B2
(45) Date of Patent: Jun. 12, 2007

(54) METHOD AND APPARATUS FOR CONTROLLING A GAS-EMITTING PROCESS AND RELATED DEVICES

(75) Inventors: John Carl Steichen, Landenberg, PA (US); Patricia A. Morris, Montchanin, DE (US); John James Barnes, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/406,970

(22) Filed: Oct. 14, 2003

(65) Prior Publication Data

US 2004/0039514 A1   Feb. 26, 2004

Related U.S. Application Data

(60) Provisional application No. 60/370,445, filed on Apr. 5, 2002.

(51) Int. Cl.
   *F02D 41/14*   (2006.01)
(52) U.S. Cl. .................. 701/109; 701/103; 123/703; 60/276; 700/32
(58) Field of Classification Search ............... 701/103, 701/109, 106, 108, 114; 123/703, 674, 704; 60/276, 278, 285; 700/32
See application file for complete search history.

(56) References Cited

U.S. PATENT DOCUMENTS

| | | | |
|---|---|---|---|
| 4,457,161 A | 7/1984 | Iwanaga | |
| 4,963,332 A | 10/1990 | Brand | |
| 5,047,220 A | 9/1991 | Polcer | |
| 5,134,080 A | 7/1992 | Bell et al. | |
| 5,233,934 A | 8/1993 | Krigmont | |
| 5,426,934 A | 6/1995 | Hunt et al. | |
| 5,427,740 A | 6/1995 | Coles | |
| 5,571,401 A | 11/1996 | Lewis | |
| 5,628,186 A | 5/1997 | Schmelz | |
| 5,680,756 A * | 10/1997 | Harima ..................... 60/274 |
| 5,783,153 A | 7/1998 | Logothetis | |
| 5,811,662 A * | 9/1998 | Williams et al. ........... 73/31.06 |
| 5,832,411 A | 11/1998 | Schatzmann | |
| 6,109,095 A | 8/2000 | Addiego | |
| 6,216,448 B1 | 4/2001 | Schnaibel et al. | |
| 6,235,243 B1 | 5/2001 | Fleischer | |
| 6,477,458 B1 * | 11/2002 | Yasui et al. ................. 701/109 |
| 6,698,186 B2 * | 3/2004 | Ueno et al. .................. 60/277 |

(Continued)

FOREIGN PATENT DOCUMENTS

| | | |
|---|---|---|
| EP | 293255 | 11/1988 |
| EP | 820799 | 1/1998 |
| WO | 93/8467 | 4/1993 |

OTHER PUBLICATIONS

International Search Report for PCT/US03/10417, dated Jul. 3, 2003.

(Continued)

*Primary Examiner*—Willis R. Wolfe, Jr.
*Assistant Examiner*—Johnny H. Hoang

(57) ABSTRACT

Disclosed herein is a method and apparatus for controlling a process, such as a chemical reaction, that emits a multi-component mixture of gases; and for controlling a device to which is transmitted a product of a chemical reaction that emits a multi-component mixture of gases.

49 Claims, 8 Drawing Sheets

U.S. PATENT DOCUMENTS

| | | |
|---|---|---|
| 6,849,239 B2 | 2/2005 | Morris |
| 6,960,476 B2 | 11/2005 | Morris |
| 2002/0017467 A1 | 2/2002 | Ando et al. |
| 2003/0037590 A1 | 2/2003 | Stark |
| 2004/0063210 A1 | 4/2004 | Staichen |
| 2004/0126286 A1 | 7/2004 | DeRuyter |

OTHER PUBLICATIONS

Ivan Arsie, Cesare Pianese and Gianfranco Rizzo, Models for the Prediction of Performance and Emissions in a Spark Ignition Engine—A Sequentially Structured Approach, SAE Paper 980779, 1998.

H. Meixner, et al., Chemosensors for motor management systems of the future, Fresenius J. Anal Chem. (1994) 348, pp. 536-541.

* cited by examiner

METHOD AND APPARATUS FOR CONTROLLING A GAS-EMITTING PROCESS AND RELATED DEVICES

FIELD OF THE INVENTION

This invention relates to methods and apparatus for controlling a process that emits a multi-component mixture of gases, or a device to which a product of a chemical reaction that emits a multi-component mixture of gases is transmitted. In particular, it relates to the use of information concerning the composition of the gases emitted by the chemical reaction for the purpose of such control.

TECHNICAL BACKGROUND

There are many examples of a process that emits a multi-component mixture of gases. One such process, combustion in an internal combustion engine, is a chemical reaction that has substantial practical importance and has consequently been studied in detail. The combustion that occurs within the cylinder of an engine is a chemical reaction in which a hydrocarbon fuel is oxidized. A multi-component mixture of gases is emitted by this reaction in the form of the engine exhaust. The products of this reaction, however, include not only the exhaust gases themselves but also the work done in moving the piston in the cylinder. Various components of an engine, including the emissions control devices, thus each acts as a device to which a product of the chemical reaction is transmitted. Although combustion of a hydrocarbon fuel is a relatively simple type of chemical reaction, the manner in which the force of the gases produced by that reaction expand against a piston to power an engine and all of its associated components is more complicated and requires control. In the case of a modern automotive engine, control is accomplished by digital processing computers in an engine control unit ("ECU") that rely on inputs from a variety of sensors and actuators.

The underlying objective of the ECU is to provide performance that optimizes fuel efficiency, drivability and reduction of harmful emissions. Signals concerning the state or condition of various operating characteristics of the engine are fed to the ECU. Typical engine operating characteristics as to which signals are inputted to the ECU are throttle position, intake manifold pressure, intake airflow, crank position, engine torque and air-to-fuel ratio (referred to as "lambda") value. Engine operating characteristics that may be adjusted for control in view of such inputs include fuel injection timing, spark advance, air-to-fuel ratio, exhaust gas recycle ("EGR") and idle air control motor. Although an engine is essentially a chemical plant oxidizing fuel with air into water, carbon dioxide and other chemical species, the only sensor currently capable of providing any information about the chemical status of the combustion process is the lambda sensor, which is limited to inferring a value for the air-to-fuel ratio of the engine based on measurements made in the stream of exhaust gases.

Much work has been done to develop relationships between the signals inputted to an ECU, and the operating characteristics that are thereby controlled, to optimize engine performance. This work is based on theoretical models of the combustion process, engine dynamics and other power train components. See, for example, Arsie, Pianese and Rizzo, *Models for the Prediction of Performance and Emissions in a Spark Ingnition Engine—A Sequentially Structured Approach*, SAE Paper 980779, 1998. Heywood, J. B., *Internal Combustion Engine Fundamentals*, McGraw Hill (1988). Pulkrabek, W. W., *Engineering Fundamentals of the Internal Combustion Engine*, Prentice Hall (1997). These models attempt to predict both the engine operating characteristics and the chemical components of the exhaust stream, but they tend to be quite complex and yield only approximate results. For this reason, an empirical system of control has been adopted that uses engine mapping.

Calibrating engine operation, either with or without an attached transmission, creates a map, which records empirically-observed relationships between one or more operating characteristics as to which information is gathered and inputted to the ECU, and one or more operating characteristics that are adjusted in view of the inputted information. For example, FIG. 4 shows a map relating speed to load to measurements concerning the presence of nitrogen oxides ($NO_x$) in the engine exhaust. It may be seen how moving along the surface defined by the map can move an engine from one operating state to another. In doing so, the value of at least one of the parameters may be held constant, if desired.

In current engine design technology, a map that includes engine exhaust gases is commonly used to estimate the emission of pollutants over a wide range of conditions. The assumption is made that the map obtained during original calibration is either stable or undergoes predictable change, in which case adaptive algorithms are used to estimate the model change. By using the relationship between input signals, controlled operating characteristics, and the mapped emission levels, engines have been operated on the assumption that the predicted relationship between mechanical performance and exhaust content is accurate, and thus that emission control of a desired nature results from control of the same operating characteristics that control mechanical performance of the engine.

It has been found, however, that control systems using engine mapping provide control only as good as the input signals and the validity of the map. As engines wear, sensors lose calibration, fuel compositions change, and the assumption made that the fundamental combustion process and the content of the exhaust stream remain stable becomes invalid. Precision analytical equipment that could provide a complete analysis of the engine exhaust gasses, and that could provide information that remains accurate during service of the engine in real time, is not practical for use for such purpose except during the original calibration of a map in a laboratory.

These deficiencies are particularly acute with respect to a map that incorporates lambda, the air-to-fuel ratio, as an input. There are two common types of lambda sensors: step-change lambda sensors and wide-range lambda sensors. The step-change lambda sensor is based on a zirconia concentration cell and operates between $\lambda=0.95$ and $\lambda=1.05$. This sensor is used for air/fuel ratio control in engines that operate around stoichiometry ($\lambda=1$). It is desirable to operate at $\lambda=1$ because the catalytic converter operates best with a stoichiometric mixture. The wide-range lambda sensor operates over a much wider range of lambda, and it enables the closed-loop control of lean-burn engines. Running lean (oxygen-rich) is important to ensure that all of the fuel is combusted.

A lambda sensor such as described above generates a single signal that indicates whether the exhaust gas is rich or lean (and in the case of the wide-range sensor, indicates to what extent rich or lean). This single signal is derived from a composite of all gases in the exhaust stream, reflecting the ratio of oxidizing to reducing gases therein. This type of lambda sensor is not capable of providing detailed information about the gas composition of an exhaust stream, and a lambda value derived from this sensor is not an indication of a unique gas composition. Different combinations of gases can produce the same lambda value. This type of lambda sensor is sometimes also referred to as an oxygen sensor because oxygen diffuses readily through the zirconia cell, but this sensor does not furnish any information about the individual concentration of oxygen as an individual component within a stream of exhaust gas. Even when a metal oxide film that has a high diffusion coefficient for oxygen is used as a lambda sensor, the resulting lambda value does not furnish useful information about the individual concentration of oxygen as an individual component within a stream of exhaust gas because the cross-sensitivity of the metal oxide film requires that assumptions be made about the extent to which other components may be present in the exhaust stream, or about the conditions under which combustion has occurred.

A lambda sensor may also be used in the monitoring and control of a nitrogen oxide ($NO_x$) absorber in a lean-burn engine. As described, for example, in U.S. Pat. No. 6,216,448, an oxygen deficiency in the exhaust gas downstream of a two part catalytic converter, which contains an upstream conventional oxygen storage section and a downstream $NO_x$ storage section, only occurs when the oxygen-storage locations as well as the nitrous oxide storage locations in the $NO_x$ storage catalytic converter are empty. These locations are emptied by the passage through them of a rich mixture. The time difference in the response of upstream and downstream sensors to the rich exhaust mixture is used as a measure of the $NO_x$, storage capacity. This is not, however, a measurement of $NO_x$ content in the exhaust gas stream.

It would therefore be desirable to have methods and apparatus for controlling a process (such as a chemical reaction) that emits a multi-component mixture of gases, or a device (such as an internal combustion engine) to which is transmitted a product of a chemical reaction that emits a multi-component mixture of gases. These methods and apparatus receive as an input, and optionally utilize in a map, information about the individual concentration within the emitted gas stream of one or more individual component gases, or subgroups of gases, therein.

SUMMARY OF THE INVENTION

One embodiment of this invention is a method for controlling a process that emits a multi-component mixture of gases by (a) providing one or more signals, each of which is related to the individual concentration within the emitted gas mixture of the same individual component gas therein, and/or the collective concentration therein of a subgroup of gases; (b) inputting the signal(s) to a decision-making routine for controlling the process; and (c) outputting a signal from the decision-making routine for adjusting an operating characteristic of the process.

A further embodiment of this invention is a method for controlling a process that emits a multi-component mixture of gases by (a) providing a decision-making routine or a map for controlling the process; (b) providing information about the composition of the emitted gas mixture to the decision-making routine or the map from an array of chemo/electro-active materials; and (c) providing an output for adjusting an operating characteristic of the process.

Another embodiment of this invention is a method for controlling a process that emits a multi-component mixture of gases by (a) providing a decision-making routine, for controlling the process, to which information is inputted from a map that relates (i) information about an operating characteristic of the process, to (ii) information about the composition of the emitted gas mixture; and (b) providing the information about the composition of the emitted gas mixture to the map on the occasion of making the decision.

Yet another embodiment of this invention is an apparatus for controlling a process that emits a multi-component mixture of gases including (a) a decision-making routine, for controlling the process, to which information is inputted from a map, and (b) a map that relates (i) information about the composition of the emitted gas mixture, which information is undetermined until the occasion of making the decision, to (ii) information about an operating characteristic of the process.

Yet another embodiment of this invention, in a chemical reaction that emits a multi-component mixture of gases, is a method of controlling the operation of a device to which a product of the chemical reaction is transmitted by (a) providing one or more signals, each of which is related to the individual concentration within the emitted gas mixture of the same individual component gas therein, and/or the collective concentration therein of a subgroup of gases; (b) inputting the signals to a decision-making routine for controlling the operation of the device; and (c) outputting a signal from the decision-making routine for adjusting an operating characteristic of the device.

Yet another embodiment of this invention, in a chemical reaction that emits a multi-component mixture of gases, is a method of controlling the operation of a device to which a product of the chemical reaction is transmitted, comprising (a) providing a decision-making routine or a map for controlling the device; (b) providing information about the composition of the emitted gas mixture to the decision-making routine or the map from an array of chemo/electro-active materials; and (c) providing an output for adjusting an operating characteristic of the device.

Yet another embodiment of this invention, in a chemical reaction that emits a multi-component mixture of gases, is a method of controlling the operation of a device to which a product of the chemical reaction is transmitted by (a) providing a decision-making routine, for controlling the device, to which information is inputted from a map that relates (i) information about an operating characteristic, to (ii) information about the composition of the emitted gas mixture; and (b) providing the information about the composition of the emitted gas mixture to the map on the occasion of making the decision.

Yet another embodiment of this invention, in a chemical reaction that emits a multi-component mixture of gas, is an apparatus for controlling the operation of a device to which a product of the chemical reaction is transmitted including (a) a decision-making routine, for controlling the device, to which information is inputted from a map, and (b) a map that relates (i) information about the composition of the emitted gas mixture, which information is undetermined until the occasion of making the decision, to (ii) information about an operating characteristic of the device. Another embodiment of this invention is the device itself, to which a product of the chemical reaction is transmitted, containing a controlling apparatus as described above.

The methods and apparatus of this invention have the ability to advantageously utilize information related to the concentration in a gas mixture of a component gas or a subgroup of gases because the information can, if desired, be (i) related to one or any number of a diverse population of gases, and/or (ii) used to calculate the actual concentration within the mixture of one or more of the individual components and/or subgroups of gases therein. Information of such extensive amount and quality can in turn be employed in a map and/or decision-making routine to adjust an operating characteristic of a process or a device.

DETAILED DESCRIPTION OF THE INVENTION

One example of the manner in which the methods and apparatus of this invention can be used to control a process such as a chemical reaction is in the control of an internal combustion engine, or components or equipment associated therewith.

Figure 5:
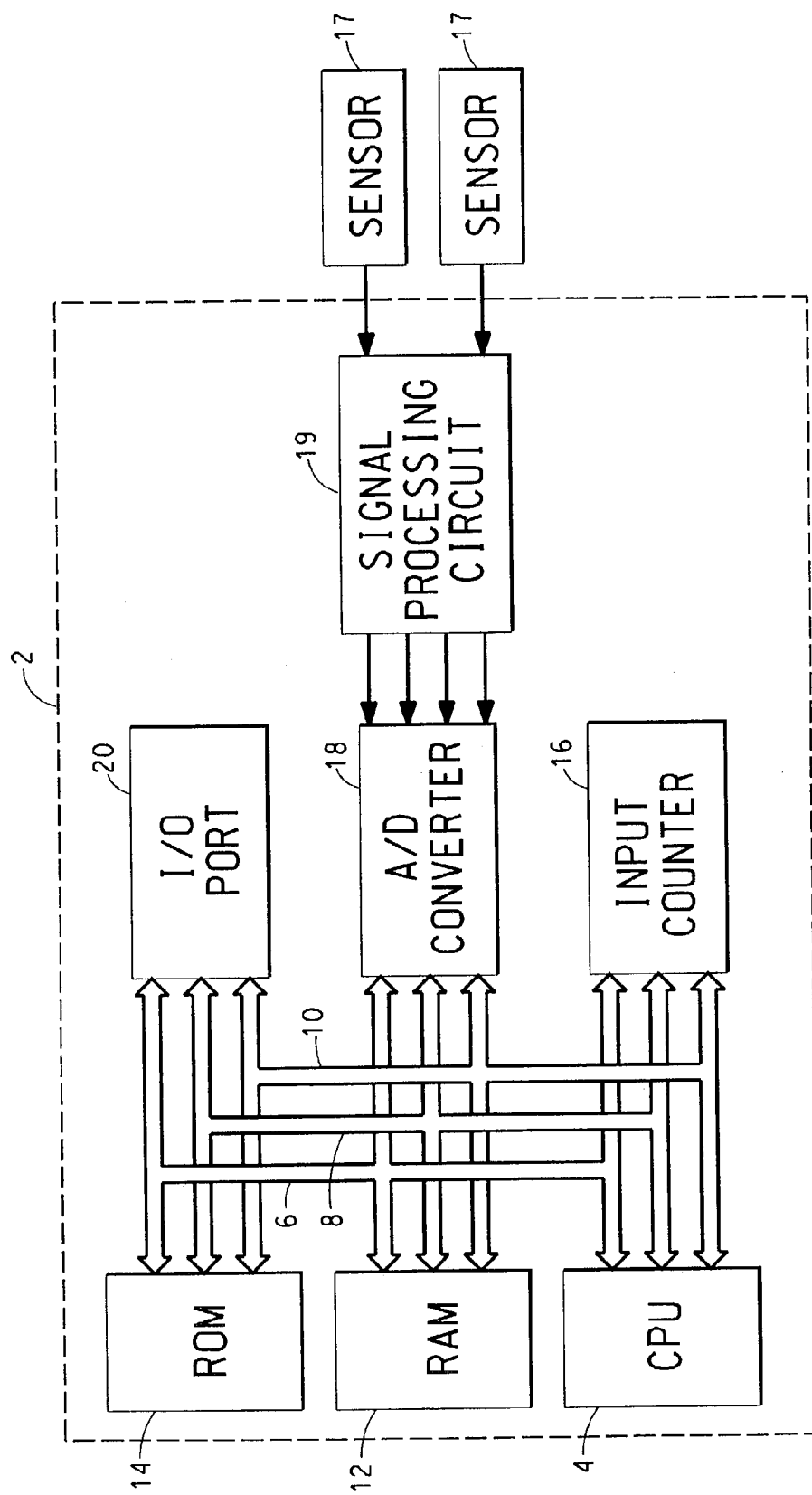
FIG. 5 is a diagram of the flow of signals into and out of the central processing unit of an engine control unit.

The operation of an internal combustion engine is typically controlled by an ECU. FIG. 5 shows in the form of a block diagram the interior construction of an ECU 2. A central processing unit, such as a microprocessor, ("CPU") 4 is connected, by way of a data bus 6, an address bus 8 and a control bus 10, to (i) a random access memory ("RAM") 12 for temporarily storing results of calculations within the CPU 4; (ii) a read-only memory ("ROM") 14 for storing a control program to be executed within the CPU 4 and a map; (iii) an input counter 16; (iv) an analog to digital (A/D) converter 18; and (v) an input/output port 20, for giving and receiving of input data and output data between the CPU 4 and the RAM 12, through the above buses. The CPU 4 performs data communication and data arithmetic operations between the ROM 14, the RAM 12 and the I/O unit 20. The ROM 14 has permanently stored therein fixed data and control programs useful in the arithmetic operations, and the RAM 12 functions to temporarily store the values obtained by the arithmetic operations. Signals are inputted from sensors 17 to signal processing circuit 19, and from there into A/D converter 18.

To control the operation of the engine, the CPU performs a multitude of decision-making routines about various operating characteristics of the engine. The CPU gathers information from sensors about the state or condition of various operating characteristics, and inputs that information to a decision-making routine. The decision-making routine applies one or more algorithms and/or mathematical operations to that information to obtain a decision in the form of a value that is equivalent to a desired state or condition that should be possessed by a particular operating characteristic. Based on the result of a decision-making routine, instructions are given by the CPU, or are controlled by the CPU, that cause a change in the state or condition of one or more operating characteristics, and thus also cause a change in the operation of the engine.

Operating characteristics about which information may be inputed to the CPU may include, for example, one or more of: battery voltage, atmospheric pressure, intake pipe negative pressure, intake air temperature, engine cooling water temperature, engine speed, engine torque, valve lift, throttle valve opening, spark advance, on-off position of the ignition or starter switch, ignition advance angle, exhaust gas recirculation ("EGR") valve opening, ratio of air to fuel supplied to the engine, and exhaust gas content. Information about these characteristics is fed to the CPU from sensors and detectors capable of measuring the mechanical and/or physical properties representative of each characteristic.

Figure 6:
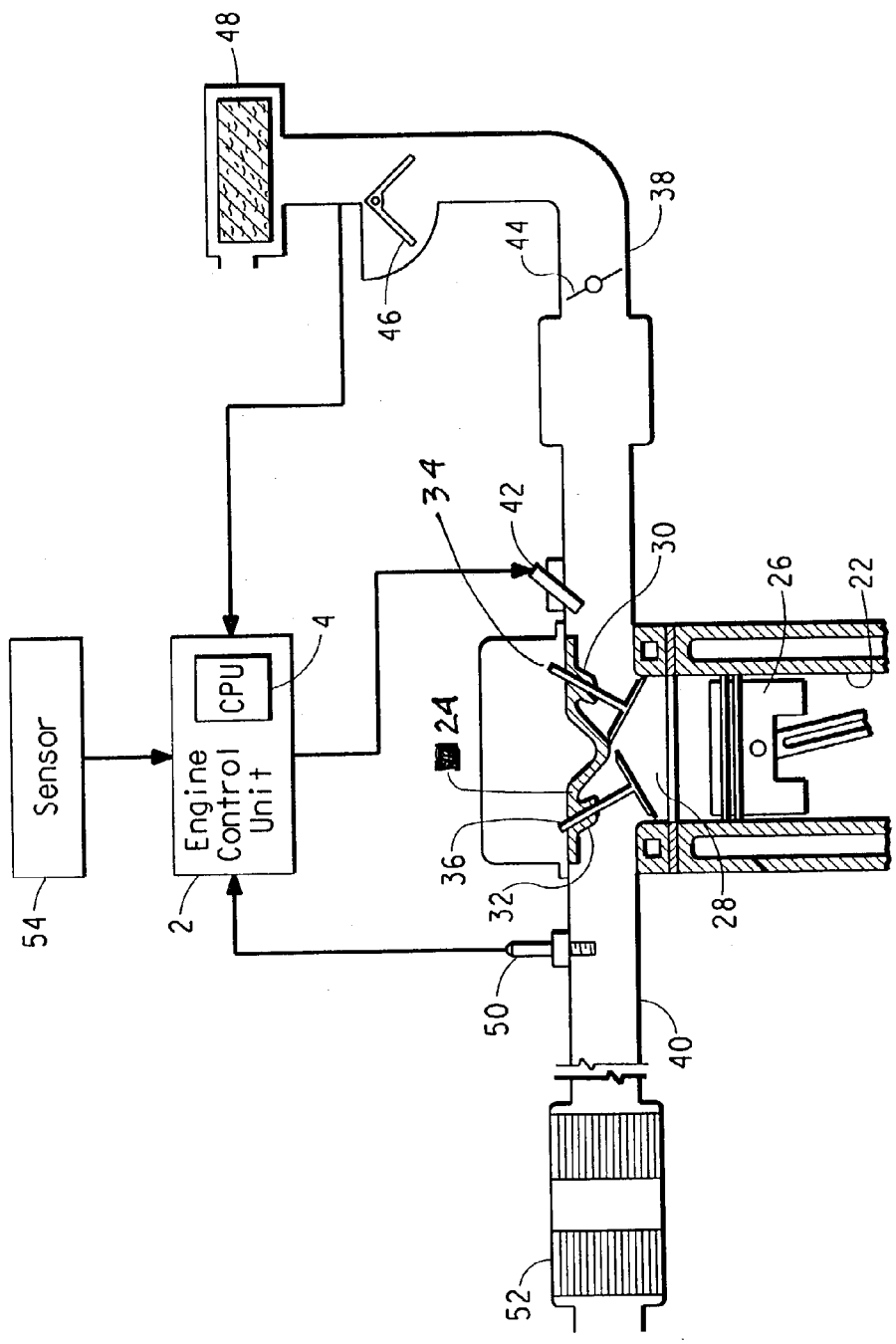
FIG. 6 is a cut-away drawing of a cylinder and associated components of an internal combustion engine.

Decisions made by the decision-making routine accessed by the CPU can be used to control the chemical reaction of combustion by, for example, adjusting the amount of fuel, and thus the air to fuel ratio, as supplied to a cylinder. A basic system to control the ratio of air to fuel as supplied to the engine is shown in FIG. 6. Shown there is an engine, including a cylinder 22 having a cylinder head 24 attached to the top end of the cylinder 22. In the cylinder 22, there is a piston 26 that reciprocates axially and defines with the cylinder 22 and the cylinder head 24 a combustion chamber 28 of variable volume. The cylinder head 24 is formed with an intake port 30 and an exhaust port 32, which are associated with an intake valve 34 and an exhaust valve 36, respectively. The intake port 30 is connected with an intake passage 38 whereas the exhaust port 32 is connected with an exhaust passage 40.

In the intake passage 38, there is provided a fuel injection valve 42 located in the vicinity of the intake port 30. The intake passage 38 further has a throttle valve 44 and an air-flow detector 46, which is located upstream of the throttle valve 44. At the upstream end of the intake passage 38, there is an air cleaner 48. In the exhaust passage 40, there is an air/fuel ratio (lambda) detector 50. Further, the exhaust passage 40 is provided with a catalytic device 52 of a type as known in the art. The engine is further provided with a sensor 54, such as an engine speed detector.

The fuel injection valve 42 is connected with a fuel supply source (not shown) and supplied with fuel under a controlled pressure. The valve 42 may be of the duty factor solenoid type in which the quantity of fuel injected through the valve 42 is determined by the duty factor of electric pulses applied to the valve 42. The CPU 4 actuates the valve 42 to control the quantity of fuel supplied to the engine, which is a parameter of the chemical reaction embodied in combustion.

The CPU 4 is connected with the outputs of sensors and detectors, preferably those that supply information about the compositional content of the exhaust gases, applies the decision-making routine to those outputs, and in turn produces output pulses that are routed to the fuel injection valve 42. The CPU 4 functions to calculate the quantity of fuel to be supplied to the engine on the basis of the engine operating condition as detected by various sensors and detectors so that a desired air-fuel ratio is established. For example, in a normal engine operating condition, it is preferred to maintain the stoichiometric air-fuel ratio, and the CPU 4 will in such case produce a basic fuel quantity signal which corresponds to the fuel quantity required for providing an air-fuel mixture of the stoichiometric ratio. The reaction of combustion may also be controlled by adjusting the amount of oxygen (or oxygen source such as air) fed to the cylinder, or adjusting the spark advance in relation to information about the compositional content of the exhaust gases.

Of equal importance is the use of the methods and apparatus of this invention to control a device to which a product of a chemical reaction is transmitted. In the case of the combustion reaction in an engine, the exhaust gas stream itself is a product of the reaction, and it is transmitted to various devices such as the exhaust gas recirculation system or a pollution abatement device such as a catalytic converter and/or a device for the storage or abatement (reduction) of $NO_x$. Information about the compositional content of the exhaust stream can be inputted from sensors and detectors to the ECU, which can utilize that information in a decision-making routine to output signals that control, for example, the settings on an exhaust recirculation valve, the extent of injection into an SCR catalytic converter of a reducing agent, or the regeneration of a $NO_x$ catalyst when contaminated with sulfur. Typical exhaust gases include oxygen, carbon monoxide, hydrogen, sulfur dioxide, ammonia, $CO_2$, $H_2S$, methanol, water, a hydrocarbon (such as $C_nH_{2n+2}$, and as same may be saturated or unsaturated, or be optionally substituted with hetero atoms; and cyclic and aromatic analogs thereof), a nitrogen oxide (such as NO, $NO_2$, $N_2O$ or $N_2O_4$) or an oxygenated carbon (CO, $CO_2$ or $C_5O_3$). In certain embodiments, gases of interest may include one or more of $NO_x$, hydrocarbons and ammonia. In certain other embodiments, however, it may be desired that the methods and apparatus not provide any signals, measurements, information or analysis with respect to oxygen.

Another product of the chemical reaction of combustion in an engine is the force generated by the reaction to do the work of moving the piston. The engine components that are powered by transmitting to them the forces produced by the chemical reaction of combustion can also be controlled by the ECU by instructions to adjust operating characteristics such as torque or engine speed.

In performing a decision-making routine, such as control of fuel supply as described above, the CPU may, and preferably does, employ a map. A map resides in the ROM 14, and is an electronic collection of information about various parameters of a chemical reaction, or information about various operating characteristics of a device to which a product or a reaction is transmitted, such as an engine. In one embodiment, a range of quantified values may be set forth within the map with respect to a particular parameter or characteristic. This could be, for example, a range of temperature between 350 and 750° C., divided into 25° C. increments. With respect to each individual value of the parameter or operating characteristic in the range set forth, the map may then associate an acceptable value for one or more other parameters or operating characteristics, or a factor to be used in a decision-making routine. A map can be established in the form of a relational database, and can be accessed by look-up instructions in a computer program.

In the performance of a decision-making routine to control the operation of an engine, a value, such as the size of an electrical signal, that is representative of the state or condition of operating characteristic A may be inputed to the CPU. In one example of how the signal can then be utilized by a decision-making routine, the CPU determines a value representative of the state or condition each of operating characteristics B and C, and reads the map to determine, in view of the values for B and C, a target value D for operating characteristic A. The target value could be a preselected value that is recorded in the map as such, or could be a value that is calculated by the CPU by a mathematical operation recorded in the map, with the calculation to specify D being made only on the occasion when the values for B and C are determined. For example, a determination may be made of the absolute value of the difference between A and B, and this absolute value, when added to C, becomes the target value D.

The value of operating characteristic A is compared to target value D, and if A is in a desired relationship to D, the CPU does not instruct the engine to make any adjustment in its operation. If A is not in a desired relationship to D, the decision-making process could, in further alternative embodiments, read the map to determine a desired value or range of values for A in terms of values for operating characteristics E and F; or calculate a desired value for A by reading the map to determine coefficients to be used in performing a mathematical operation on E and F. The values for E and F could be determined at the time of making the decision, or could be preselected values stored in the map. In either case, once the desired value for A is determined, the CPU instructs the necessary operating characteristics of the engine to be adjusted in the manner necessary to obtain the desired value for A. This may be done by adjusting operating characteristic A itself, or adjusting other operating characteristics that can influence the state or condition of A.

In like manner, a chemical reaction may be controlled by a decision-making routine that receives inputs, preferably from a map, and generates outputs in view of such inputs to adjust one or more parameters of the reaction.

In this invention, information about the compositional content of the gas emitted by a chemical reaction, such as the exhaust gas of an engine, is used as an input to a decision-making process that controls the chemical reaction, or controls the operation of a device to which a product of the reaction has been transmitted. In the example described above, information about the exhaust gas of the engine could be used as the representative value that is inputed with respect to any one or more of operating characteristics A, B, C, E or F, or could be used as a coefficient in a operation that the decision-making routine causes to be performed. Information about the gas composition is inputed to the decision-making routine, in this invention, in the form of one or more signals that is or are related to the individual concentration within the emitted gas stream of a particular individual component gas therein, or a particular subgroup of some but not all of the component gases therein, or both individual component(s) and subgroup(s). The relationship may be a mathematical relationship, such as a monotonic relationship, involving for example a log, inverse or scaled value. This is accomplished by exposing an array of chemo/electro-active materials to the emitted gas stream to generate a signal that may be, for example, an electrical or optical signal.

For example, in a method for controlling a process that emits a multi-component mixture of gases, or in a chemical reaction that emits a multi-component mixture of gases where there is a method of controlling the operation of a device to which a product of the chemical reaction is transmitted, it is possible to provide one or more signals, such as first and second signals, each of which is related to (i) the individual concentration within the emitted gas mixture of the same individual component gas, such as first and second individual component gases, and/or (ii) the collective concentration within the emitted gas mixture of a subgroup of the component gases therein. The signal or signals are then inputted into a decision-making routine for controlling the process; and a signal is outputted from the decision-making routine for adjusting an operating characteristic of the process or device. The number of signals, if more than one, may be any desired number such as 2 or more, 4 or more, 6 or more, 8 or more, 10 or more or 12 or more. In a preferred embodiment, the signal is proportional to the resistance of a chemo/elelctro-active material that has been exposed to the gas mixture. Although this signal may be subjected to operations such as inversion, scaling or log function, the signal is preferably utilized without any computation involving coefficients, factors or other values, such as in an algorithm.

The ability to furnish information about the individual concentration within an emitted gas stream of a particular component gas or subgroup therein makes it possible to calibrate a map. When building a map before a reaction or device to be controlled is put into service, values representative of a variety of parameters or operating characteristics must be determined by systematically operating the reaction or device under a large enough sample of different conditions to approximate all the conditions expected in actual service. An array of chemo/electro-active materials can be used to analyze the composition of the emitted gas stream to furnish information based on the concentration of individual components or subgroups therein to be recorded in the map in relation to values of other parameters or operating characteristics measured under the same operating conditions.

If desired, however, this ability to furnish information related to the concentration of individual components or subgroups in an emitted gas stream can be used to calibrate or re-calibrate a map in real time while the reaction or device is in service. For example, a relationship could be established in a map between a value representative of the concentration of an individual gas component or subgroup, and values representative of various parameters or operating characteristics, with the value for the gas concentration to be supplied in real time. This might take the form of a decision-making routine involving a mathematical operation in which a value representative of the concentration of an individual gas component or subgroup is used as a factor or coefficient. The value representative of the concentration of an individual gas component or subgroup could remain undetermined until the time that the mathematical operation is performed in the execution of the decision-making routine to make the decision. The value representative of the concentration of an individual gas component or subgroup is determined and supplied to the decision-making routine only on the occasion of making the decision, and the decision thus need not be made based on information that may not be currently accurate at the time the decision is made. A map in which one or more parameters or operating characteristics is related to information about the concentration of an individual gas component or subgroup, with the information about the gas concentration being furnished in real time while a reaction or device is in service, clearly then has substantial value because it is possible to essentially recalibrate the map continually in real time.

In this invention, information about an emitted gas composition may be supplied to a map from an apparatus employing one or more chemo/electro-active materials that furnishes an analysis of the emitted gas stream. Responses generated by the apparatus are then typically used without manipulation as inputs to a map, optionally along with the input from other sensors, and are matched or compared by the map to previously stored values that are representative of various different conditions of operation. In alternative embodiments, however, the values may be subjected to the manipulation by an algorithm to further refine the control of a reaction, or of a device to which a product of the reaction has been transmitted.

In the case again of an engine, there are several ways in which an apparatus containing one or more chemo/electro-active materials can be incorporated into the operation of the ECU to control the combustion reaction or the engine. The chemo/elctro-active materials may be constructed as an array of sensors that have sensitivity to individual gaseous components or subgroups of gases in the exhaust stream. Such sensors can be fabricated from semiconducting materials that respond uniquely to individual gases or gas subgroups that have common characteristics such as similar oxidation potential, electronegativity, or ability to form free radicals. These are properties of interest when characterizing combustion. Typical examples of a subgroup of gases within an exhaust stream are the hydrocarbons or the nitrogen oxides. The responses of an array of chemo/electro-active materials to the multi-component mixture of gases formed by a stream of exhaust can thus be used to characterize the current status of the combustion reaction in an engine.

Figure 7:
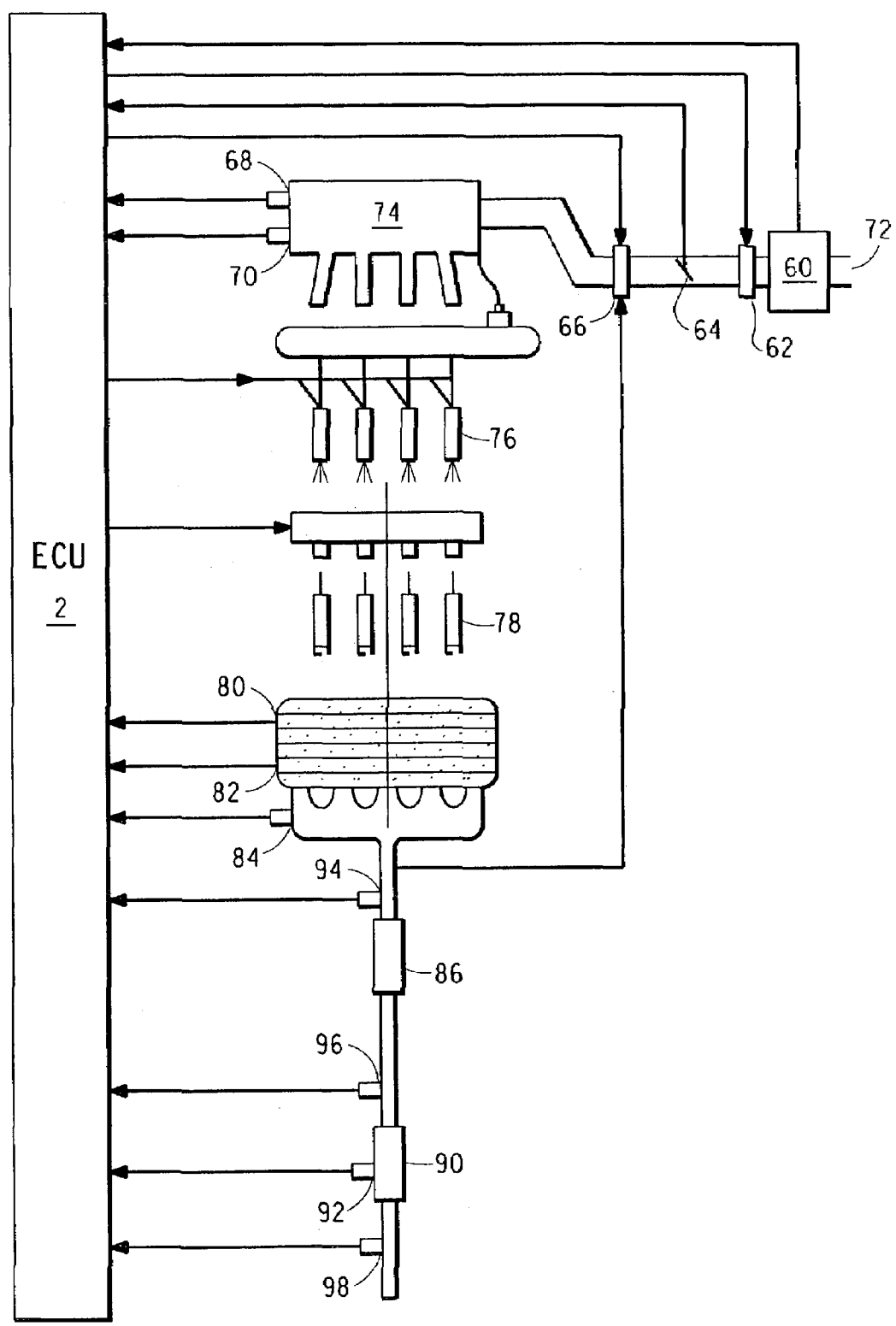
FIG. 7 is a schematic layout of an internal combustion engine showing the placement therein of an array of gas sensors.
Figure 8:
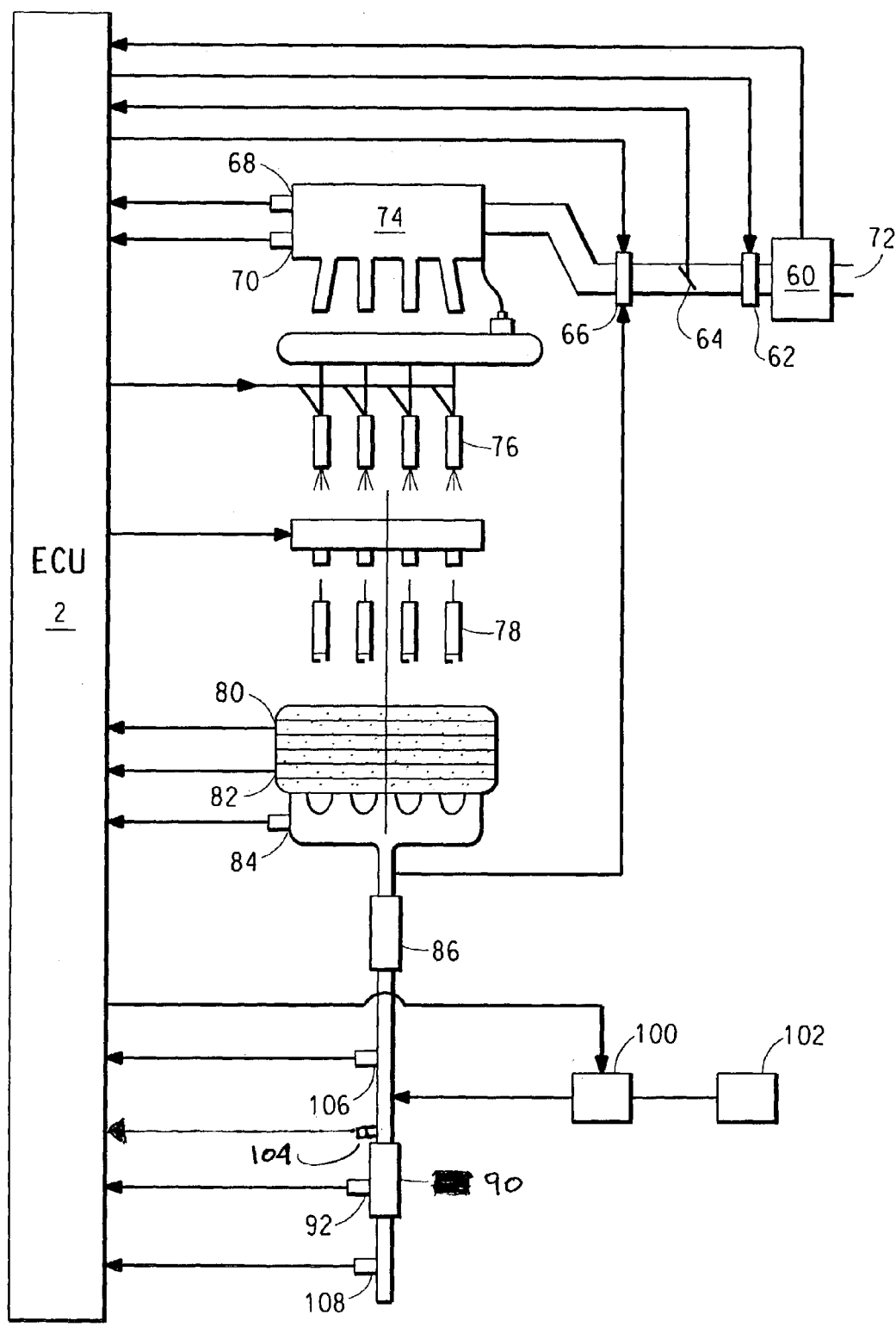
FIG. 8 is a schematic layout of an internal combustion engine showing the placement therein of an array of gas sensors.

FIGS. 7 and 8 show several possible locations of an array of sensor materials in an exhaust system. The engine in FIGS. 7 and 8 contains a mass airflow and outside temperature sensor 60, an idle air valve 62, a throttle position valve 64, an exhaust gas recycle valve 66, an air temperature sensor 68, a pressure sensor 70, an air intake 72, an intake manifold 74, fuel injectors 76, spark plugs 78, a crank position sensor 80, a cam position sensor 82, a coolant temperature sensor 84, a pre-catalytic converter 86, an emissions control device (such as a catalytic converter and/or a device for the storage or abatement of $NO_x$) 90, and a temperature sensor 92. FIG. 7 shows three possible locations 94, 96, 98 for an array of chemo/electro-active materials, which may be upstream or downstream from the emissions control device. The arrows indicate the locations where it would be possible, if desired, to provide for the flow of information to/from the ECU to/from one or more sensors or acctuators. Information gathered from an array of chemo/electro-active materials and processed by the ECU could be used, for example, to control the exhaust gas recycle valve 66 or the fuel injectors 76.

An array in position 94 is located close to engine and responds directly to the exhaust from individual cylinders. Because of its proximity and fast response, the array in this location can be used to control the operation of each individual cylinder. An array in this location is exposed to very high exhaust temperatures for which semiconducting sensor materials are very suitable. An array in position 96 in FIG. 7 operates cooler and is exposed to gasses that have already been modified in composition by the precatalyst. However, the gas stream at this point still contains much chemical information that can be used by the ECU for engine control. This is also a suitable location to employ feed-forward control by using an array of sensor materials to control operation of the catalytic converter, which catalyzes the completion of the oxidation of unburned fuel. Position 98 is a location that can be used to monitor engine emissions and the current state of the catalytic converter. Based on information from an array at this location, the catalytic converter can be regenerated or otherwise controlled through feedback process control.

The emissions control device 90 may be a device for the storage or abatement of $NO_x$ such as a selective catalytic reduction ("SCR") converter. When an SCR converter is used to abate $NO_x$, a reducing agent such as ammonia or urea is contacted with the NOx in the gas stream, and the catalyzed reaction thereof yields nitrogen and water. FIG. 8 shows the deployment of an array of sensors in a control system using an SCR converter. Sensors in this arrangement can be used either for feed-forward (position 104 or 106) or feedback (position 108) control. As the array of sensors would be responsive to ammonia, the control system can be used to detect and minimize the emission of both nitrogen oxides and ammonia that pass unreacted through the catalyst bed, the latter being a condition known as ammonia slip. A reservoir 102 and pump 100 are provided for injection of the reducing agent into the stream of flowing gas.

An internal combustion engine and its associated components and equipment, controlled by the methods and apparatus of this invention, can be used for many different purposes including, for example, as a power source in any type of vehicle for transportation or recreation such as a car, truck, bus, locomotive, aircraft, spacecraft, boat, jet ski, all-terrain vehicle or snowmobile; or in equipment for construction, maintenance or industrial operations such as pumps, lifts, hoists, cranes, generators, or equipment for demolition, earth moving, digging, drilling, mining or groundskeeping.

Although this invention has been described in detail with respect to the control of an internal combustion engine, this invention is not limited thereto, and may be readily used in a substantially similar manner to control a device other than an engine to which a reaction product is transmitted. Other such devices include a steam boiler as used for example in a furnace or for power generation. In some of these devices, a reaction product of interest that is transmitted to the device may be the energy that is released as heat by the exotherm inherent in the burning of a fossil fuel such as coal or natural gas. For example, the setting on a steam valve on a boiler could be adjusted in view of information about the compositional content of the gas mixture emitted by the burner by which the boiler is heated. In a cogeneration plant in which waste is incinerated, the reaction product of interest may be the mixture of gases emitted by the burning of fuels and/or wastes. The mixture of gases is transmitted to a device such as a scrubber in a stack, and the scrubbing device may be controlled for pollution abatement in view of the compositional content of the mixture of gases upstream and/or downstream from the scrubber.

The methods and apparatus of this invention may also be used to control a gas-emitting process by adjusting an operating characteristic thereof. A particular kind of such process is a chemical reaction that emits a multi-component mixture of gases. Such a reaction may be controlled by adjusting, as the operating characteristic, a parameter of the reaction. The adjustment may be made in view of information about the compositional content of the mixture of gases. As noted above, the reaction of combustion can be controlled by adjusting a parameter thereof such as the amount of fuel supplied. For other kinds of reactions, parameters that may be adjusted include reactant concentration as determined by rate of reactant feed, rate of feed of a recycle stream containing unreacted reactants, or routing the recycle stream through, or bypassing, a purification step before return to the reactor;

thermal conditions, as regulated by heat transfer through a heat exchanger, or a change of volume or pressure;

pressure regulation by adjustment of settings on vents;

catalytic conditions, as regulated by rate of movement of a moving bed, or frequency of catalyst regeneration;

residence time distribution, as regulated by length of time in a batch vessel, or routing through or bypassing optional sections of a pipe reactor; or flow pattern in a reactor, as regulated by rate of stirring, rate of pumparound, rate of agitation by bubbles or liquid spray, or routing through or bypassing in-line mixers.

Other illustrative chemical reactions that may be controlled in view of information about the compositional content of a mixture of gases emitted therefrom include the production of syngas by partial oxidation of natural gas, which is an important route to a wide range of hydrocarbons. The primary benefit of this process is that it enables "stranded gas", i.e. natural gas in remote areas, to be converted to a liquid form for easy transport. In partial oxidation, natural gas is reacted with oxygen over a catalyst to form CO and $H_2$. Feedback control, based on the measurement of CO and $H_2$ would be very useful in adjusting the feed of the mixture of air and natural gas. In this way, it would be possible to compensate for changes in the activity of the catalyst by changing the mixture or the total flow.

The production of HCN is an important step in the production of adipic acid for nylon. HCN is produced by the Andrussow process where natural gas, air (or oxygen), and ammonia are reacted over a catalyst. The products are HCN, water vapor and unreacted species. Feedback control, based on compositional analysis of the product mix, could enable adjustments in the reactant mix, preheating temperature of the reactants, and total flow. This process is highly susceptible to changes in the activity of the catalyst, and diagnosis of these changes and compensating adjustments for them may be achieved by analyzing the product composition.

The heat treating of steels is performed primarily in carburizing environments, such as $H_2/CO$ mixtures. Heat treating occurs in furnaces at very high temperatures. It is vital in this reactive environment to maintain a constant gas composition to ensure that the carbon activity and oxygen activity are constant. This ensures the consistency in the quality of the steel that is being treated. Gas sensors may be used to provide rapid feedback control to the furnace environment by adjustment of gas content.

The Claus process is used to produce solid sulfur from $H_2S$ in natural gas. $H_2S$ is removed from the natural gas with ethanolamine with which it forms a complex at lower temperatures. After separation from the natural gas, the ethanolamine is heated to drive off the $H_2S$. The $H_2S$ stream is then partially oxidized to $SO_2$. The $H_2S$ and $SO_2$ are then reacted to form water and liquid sulfur. The critical analytical phase of this process is the measurement of $H_2S$ and $SO_2$ blend to be sure that it is at a stoichiometric ratio. An array of chemo/electro-active materials could measure the concentration of both gasses, with adjustments to the amount of either gas being made as needed to obtain or maintain the desired ratio.

The reaction between hydrogen or methanol and oxygen, or a source of oxygen, in a fuel cell may be controlled by analyzing the stream of gases emitted from the cell, such as $CO_2$, CO, hydrogen, $H_2S$, $SO_2$ and ammonia. The reaction may be controlled by adjusting the rate of feed of reactants.

In addition to a chemical reaction, the methods and apparatus of this invention may also be used to control a biochemical reaction that emits a multi-component mixture of gases. A biochemical reaction is one in which some or all of the reactants or products are single- or multi-cellular organisms. As with a chemical reaction, a biochemical reaction may be controlled by adjusting, as the operating characteristic, a parameter of the reaction. The adjustment may be made in view of information about the compositional content of the mixture of gases emitted by the reaction.

In fermentation, for example, optimum conditions are achieved only within narrow ranges of operation. Depending upon the type of process, nutrient levels must be optimized along with that of oxidants. Analysis of emitted gases with an apparatus located in the headspace of a fermenter is useful for control purposes because such an apparatus may be sterilized along with all other parts of the reactor prior to charging. A typical set of headspace analytes might be oxygen, carbon dioxide and xylene. Parameters of a biochemical reaction that may be adjusted include temperature, rate of stirring, degree of agitation by sparger or bubbles, pH, residence time, rate supply of oxygen, rate of supply of antifoam agent, or optional sterilization by heating or filtration of reactants upon charging.

A gas-emitting process that is not a chemical or biochemical reaction may also be controlled by adjusting an operating parameter thereof. For example, simple but accurate gas blending is a requirement in many industries. Such gas blending is needed for the etching and deposition gasses used in the electronic semiconductor fabrication industry, and for the blending of either methyl bromide or ethylene dioxide in sterilization gasses. Analysis of the compositional content of such gas mixtures enables control of the blending process by adjustment of the relative amounts of the gases present in the blending process.

In the recovery of a solid product from a synthesis reaction, a drying or devolatilization process is often employed. Control of the recovery process may be accomplished in view of information about the compositional content of the offgassing. This control may be effected by adjusting an operating characteristic of the drying process such as the feed rate to a dryer, residence time in a dryer or temperature of a dryer. Characteristics such as the following may be adjusted:

- speed of or size of load of a continuous tray dryer, as in a tunnel dryer;
- pressure with which a drying medium passes through a screen-bottom, through-circulation dryer;
- direction of flow of a drying medium: co-, counter- or cross-current, for example in a drying column; or
- speed of rotation of a drum dryer, of the plows on a continuous plate dryer, or the screw in a conical mixer dryer.

Distillation also may used for product recovery, as well as other purposes, and analysis of the compositional content of the vapors at the top of the column may be used to control the distillation process. Operating characteristics of distillation that could be adjusted in view of information obtained from gas analysis include reflux ratio, re-routing of feed to optional points of entry on the column, and vapor pressure.

In this invention, in a method for controlling a process that emits a multi-component mixture of gases, or in a chemical reaction that emits a multi-component mixture of gases where there is a method of controlling the operation of a device to which a product of the chemical reaction is transmitted, a decision-making routine may be provided, for controlling the process or the device, that receives as an input information about the composition of the emitted gas mixture. The inputted information about the composition of the emitted gas mixture may be provided from an array of chemo/electro-active materials; and, after the information has been provided as an input, there may be an output from the decision-making routine for adjusting an operating characteristic of the process or device. If desired as an alternative or in addition, a map may be provided that relates information about the composition of the emitted gas mixture to an operating characteristic of the process or device, and the information about the composition of the emitted gas mixture is provided to the map from an array of chemo/electro-active materials. It is then possible to provide information from the map to a decision-making routine for adjusting an operating characteristic of the process or device.

In the present invention, an array of chemo/electro-active materials is thus used for the purposes described above to direct sensing one or more analyte gases in a multi-component gas system under variable temperature conditions. By "directly sensing" is meant that an array of gas-sensing materials will be exposed to a mixture of gases that constitutes a multi-component gas system, such as in a stream of flowing gases. The array may be situated within the gas mixture, and more particularly within the source of the gas mixture, if desired. Alternatively, the array may reside in a chamber to which the gas mixture is directed from its source at another location. When gas is directed to a chamber in which an array is located, the gas mixture may be inserted in and removed from the chamber by piping, conduits or any other suitable gas transmission equipment.

A response may be obtained upon exposure of the gas-sensing materials to the multi-component gas mixture, and the response will be a function of the concentrations of one or more of the analyte gases themselves in the gas mixture. The sensor materials will be exposed simultaneously (or substantially simultaneously) to each of the analyte gases, and an analyte gas does not have to be physically separated from the multi-component gas mixture to be able to conduct an analysis of the mixture and/or one or more analyte components thereof. This invention can be used, for example, to obtain responses to, and thus to detect and/or measure the concentrations, of combustion gases, such as oxygen, carbon monoxide, nitrogen oxides, hydrocarbons such as butane, $CO_2$, $H_2S$, sulfur dioxide, halogens, hydrogen, water vapor, an organo-phosphorus gas, and ammonia, at variable temperatures in gas mixtures such as automobile emissions.

Figure 1:
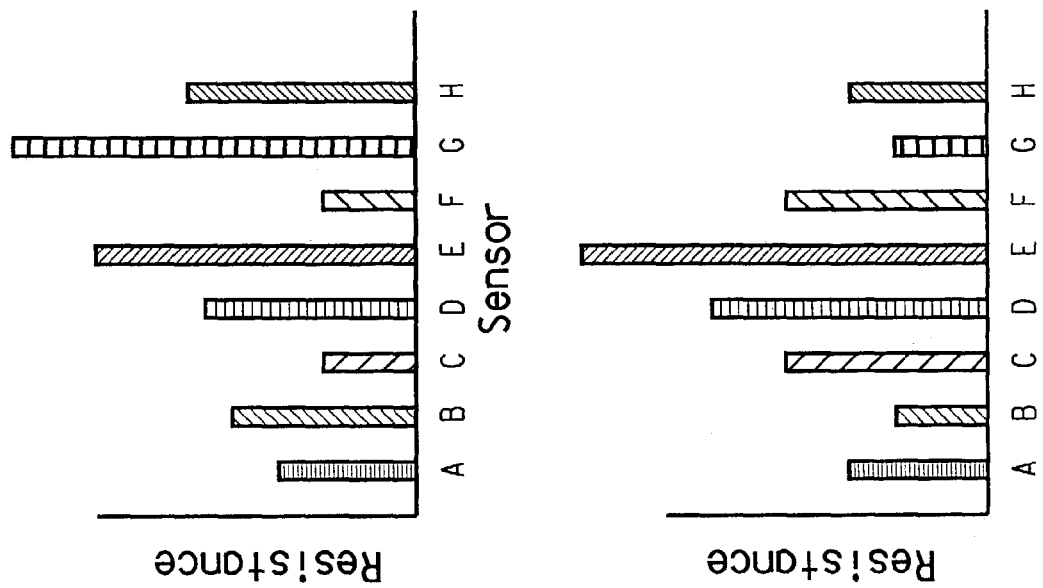
FIG. 1 depicts an array of chemo/electro-active materials.
Figure 1:
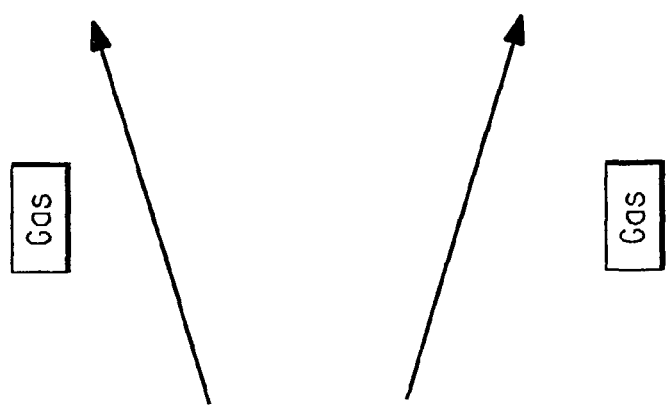
Figure 1:
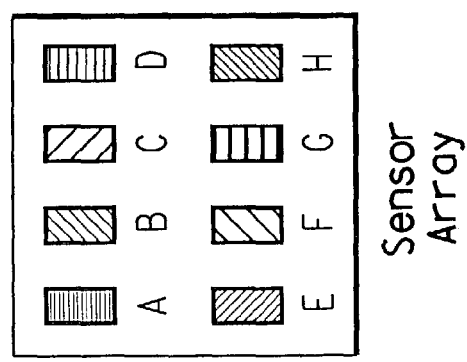

This invention utilizes an array of sensing materials to analyze a gas mixture and/or the components thereof to, for example, obtain a response to, detect the presence of and/or calculate the concentration of one or more individual analyte gas components in the system. By "array" is meant at least two different materials that are spatially separated, as shown for example in FIG. 1. The array may contain, for example, 3, 4, 5, 6, 8, 10 or 12 gas-sensing materials, or other greater or lesser numbers as desired. It is preferred that there be provided at least one sensor material for each of the individual gases or subgroups of gases in the mixture to be analyzed. It may be desirable, however, to provide more than one sensor material that is responsive to an individual gas component and/or a particular subgroup of gases in the mixture. For example, a group of at least 2, 3, 4, 5, 6, 7, 8, 9, 10, 11 or 12 sensors could be used to detect the presence of, and/or calculate the concentration of, one or more individual component gases and/or one or more subgroups of gases in the mixture. Groups of sensors, which may or may not have members in common, could be used to obtain a response to an analyte that is an individual gas component or a subgroup of gases in the mixture. A subgroup of gases that is, as the subgroup, an analyte may or may not contain as a member an individual gas that is itself also an analyte.

This invention is useful for detecting those gases that are expected to be present in a gas stream. For example, in a combustion process, gases that are expected to be present include oxygen, nitrogen oxides (such as NO, $NO_2$, $N_2O$ or $N_2O_4$), carbon monoxide, hydrocarbons (such as $C_nH_{2n+2}$, and as same may be saturated or unsaturated, or be optionally substituted with hetero atoms; and cyclic and aromatic analogs thereof), ammonia or hydrogen sulfide, sulfur dioxide, $CO_2$, or methanol. Other gases of interest may include alcohol vapors, solvent vapors, hydrogen, water vapor, and those deriving from saturated and unsaturated hydrocarbons, ethers, ketones, aldehydes, carbonyls, biomolecules and microorganisms. The component of a multi-component gas mixture that is an analyte of interest may be an individual gas such as carbon monoxide; may be a subgroup of some but not all of the gases contained in the mixture, such as the nitrogen oxides ($NO_x$) or hydrocarbons; or may be a combination of one or more individual gases and one or more subgroups. When a subgroup of gases is an analyte, a chemo/electro-active material will respond to the collective concentration within a multi-component gas mixture of the members of the subgroup together.

The analyte gas(es) contained in the mixture to which the chemo/electro-active material will be exposed can be a single gas, a subgroup of gases together, or one or more gases or subgroups mixed with an inert gas such as nitrogen. Particular gases of interest are donor and acceptor gases. These are gases that either donate electrons to the semiconducting material, such as carbon monoxide, $H_2S$ and hydrocarbons, or accept electrons from the semiconducting material, such as $O_2$, nitrogen oxides (commonly depicted as $NO_x$), and halogens. When exposed to a donor gas, an n-type semiconducting material will have a decrease in electrical resistance, increasing the current, and it, therefore, will show an increase in temperature due to $I^2R$ heating. When exposed to an acceptor gas, an n-type semiconducting material will have an increase in electrical resistance, decreasing the current, and therefore will show a decrease in temperature due to $I^2R$ heating. The opposite occurs in each instance with p-type semiconducting materials.

Obtaining information related to the compositional content of a gas mixture using these sensor materials, such as measurement of gas concentrations, can be based on a change in an electrical property, such as AC impedance, of at least one, but preferably each and all, of the materials upon exposure of the materials to a mixture containing one or more analyte gases. Analysis of a gas mixture can also be performed in terms of extent of change in other electrical properties of the sensor materials, such as capacitance, voltage, current or AC or DC resistance. Change in DC resistance may be determined, for example, by measuring change in temperature at constant voltage. The change in one of these illustrative properties of a sensor material is a function of the partial pressure of an analyte gas within the gas mixture, which in turn determines the concentration at which the molecules of the analyte gases become adsorbed on the surface of a sensor material, thus affecting the electrical response characteristics of that material. By using an array of chemo/electro-active materials, a pattern of the respective responses exhibited by the materials upon exposure to a mixture containing one or more analyte gases can be used to simultaneously and directly detect the presence of, and/or measure the concentration of, at least one gas in a multi-component gas system. The invention, in turn, can be used to determine the composition of the gas system. The concept is illustrated schematically in FIG. 1 and is exemplified below.

To illustrate, consider the theoretical example below of the exposure of a sensor material to a mixture containing an analyte gas. Where a response is obtained, the event is depicted as positive (+), and where no response is obtained, the event is depicted as negative (−). Material 1 responds to Gas 1 and Gas 2, but shows no response to Gas 3. Material 2 responds to Gas 1 and Gas 3, but shows no response to Gas 2, and Material 3 responds to Gas 2 and Gas 3, but shows no response to Gas 1.

|  | Material 1 | Material 2 | Material 3 |
|---|---|---|---|
| Gas 1 | + | + | − |
| Gas 2 | + | − | + |
| Gas 3 | − | + | + |

Therefore, if an array consisting of Materials 1, 2 and 3 gives the following response to an unknown gas,

|  | Material 1 | Material 2 | Material 3 |
|---|---|---|---|
| Unknown Gas | + | − | + | then the unknown gas would be identified as Gas 2. The response of each sensor material would be a function of the partial pressure within the mixture of, and thus the concentration of, an analyte gas or the collective concentration of a subgroup of analyte gases; and the response could be quantified or recorded as a processible value, such as a numerical value. In such case, the values of one or more responses can be used to generate quantitative information about the presence within the mixture of one or more analyte gases. In a multicomponent gas system, chemometrics, neural networks or other pattern recognition techniques could be used to calculate the concentration of one or more analyte gases in the mixture of the system.

The sensing materials used are chemo/electro-active materials. A "chemo/electro-active material" is a material that has an electrical response to at least one individual gas in a mixture. Some metal oxide semiconducting materials, mixtures thereof, or mixtures of metal oxide semiconductors with other inorganic compounds are chemo/electro-active, and are particularly useful in this invention. Each of the various chemo/electro-active materials used herein preferably exhibits an electrically-detectable response of a different kind and/or extent, upon exposure to the mixture and/or an analyte gas, than each of the other chemo/electro-active materials. As a result, an array of appropriately chosen chemo/electro-active materials can be used to analyze a multi-component gas mixture, such as by interacting with an analyte gas, sensing an analyte gas, or determining the presence and/or concentration of one or more analyte gases or subgroups in a mixture, despite the presence therein of interfering gases that are not of interest. Preferably the mole percentages of the major components of each gas-sensing material differs from that of each of the others.

The chemo/electro-active material can be of any type, but especially useful are semiconducting metal oxides such as $SnO_2$, $TiO_2$, $WO_3$ and ZnO. These particular materials are advantageous due to their chemical and thermal stability. The chemo/electro-active material can be a mixture of two or more semiconducting materials, or a mixture of a semiconducting material with an inorganic material, or combinations thereof. The semiconducting materials of interest can be deposited on a suitable solid substrate that is an insulator such as, but not limited to, alumina or silica and is stable under the conditions of the multi-component gas mixture. The array then takes the form of the sensor materials as deposited on the substrate. Other suitable sensor materials include single crystal or polycrystalline semiconductors of the bulk or thin film type, amorphous semiconducting materials, and semiconductor materials that are not composed of metal oxides.

The chemo/electro-active materials that contain more than one metal do not have to be a compound or solid solution, but can be a multi-phase physical mixture of discrete metals and/or metal oxides. As there will be varying degrees of solid state diffusion by the precursor materials from which the chemo/electro-active materials are formed, the final materials may exhibit composition gradients, and they can be crystalline or amorphous. Suitable metal oxides are those that i) when at a temperature of about 400° C. or above, have a resistivity of about 1 to about $10^6$ ohm-cm, preferably about 1 to about $10^5$ ohm-cm, and more preferably about 10 to about $10^4$ ohm-cm;

ii) show a chemo/electro response to at least one gas of interest; and iii) are stable and have mechanical integrity, that is are able to adhere to the substrate and not degrade at the operating temperature.

The metal oxides may also contain minor or trace amounts of hydration and elements present in the precursor materials.

The sensor materials may optionally contain one or more additives to promote adhesion to a substrate, or that alter the conductance, resistance or selectivity of the sensor material. Examples of additives to alter the conductance, resistance or selectivity of the sensor material include Ag, Au or Pt, as well as frits. Examples of additives to promote adhesion include frits, which are finely ground inorganic minerals that are transformed into glass or enamel on heating, or a rapidly quenched glass that retains its amorphous quality in the solid state. Frit precursor compounds are melted at high temperature and quenched, usually by rapidly pouring the melt into a fluid such as water, or by pouring through spinning metal rollers. The precursor compounds usually are a mechanical mixture of solid compounds such as oxides, nitrates or carbonates, or can be co-precipitated or gelled from a solution. Suitable precursor materials for frits include alkali and alkaline earth alumino-silicates and alumino-boro-silicates, copper, lead, phosphorus, titanium, zinc and zirconium. Frits as additives may be used in amounts of up to 30 volume percent, and preferably up to 10 volume percent, of the total volume of the chemo/electro-active material from which the sensor is made.

If desired, the sensor materials may also contain additives that, for example, catalyze the oxidation of a gas of interest or promote the selectivity for a particular analyte gas; or contain one or more dopants that convert an n semiconductor to a p semiconductor, or vice versa. These additives may be used in amounts of up to 30 weight percent, and preferably up to 10 weight percent, of the chemo/electro-active material from which the sensor is made.

Any frits or other additives used need not be uniformly or homogeneously distributed throughout the sensor material as fabricated, but may be localized on or near a particular surface thereof as desired. Each chemo/electro-active material may, if desired, be covered with a porous dielectric overlayer.

The chemo/electro-active materials used as sensor materials in this invention may, for example, be metal oxides of the formula $M^1O_x$, $M^1_aM^2_bO_x$, or $M^1_aM^2_bM^3_cO_x$; or mixtures thereof, wherein $M^1$, $M^2$ and $M^3$ are metals that form stable oxides when fired in the presence of oxygen above 500° C.;

$M^1$ is selected from Periodic Groups 2–15 and the lanthanide group;

$M^2$ and $M^3$ are each independently selected from Periodic Groups 1–15 and the lanthanide group;

$M^1$ and $M^2$ are not the same in $M^1_aM^2_bO_x$, and $M^1$, $M^2$ and $M^3$ are not the same in $M^1_aM^2_bM^3_cO_x$;

a, b, and c are each independently in the range of about 0.0005 to about 1; and x is a number sufficient so that the oxygen present balances the charges of the other elements present in the chemo/elelctro-active material.

In certain preferred embodiments, the metal oxide materials may include those in which $M^1$ is selected from the group consisting of Ce, Co, Cu, Fe, Ga, Nb, Ni, Pr, Ru, Sn, Ti, Tm, W, Yb, Zn, and Zr; and/or $M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr;

but in which $M^1$ and $M^2$ are not the same in $M^1_aM^2_bO_x$, and $M^1$, $M^2$ and $M^3$ are not the same in $M^1_aM^2_bM^3_cO_x$.

In certain other preferred embodiments, the metal oxide materials may include those in which $M^1O_x$ is $CeO_x$, $CoO_x$, $CuO_x$, $FeO_x$, $GaO_x$, $NbO_x$, $NiO_x$, $PrO_x$, $RuO_x$, $SnO_x$, $TaO_x$, $TiO_x$, $TmO_x$, $WO_x$, $YbO_x$, $ZnO_x$, $ZrO_x$, $SnO_x$ with Ag additive, $ZnO_x$ with Ag additive, $TiO_x$ with Pt additive, $ZnO_x$ with frit additive, $NiO_x$ with frit additive, $SnO_x$ with frit additive, or $WO_x$ with frit additive; and/or $M^1_aM^2_bO_x$ is $Al_aCr_bO_x$, $Al_aFe_bO_x$, $Al_aMg_bO_x$, $Al_aNi_bO_x$, $Al_aTi_bO_x$, $Al_aV_bO_x$, $Ba_aCu_bO_x$, $Ba_aSn_bO_x$, $Ba_aZn_bO_x$, $Bi_aRu_bO_x$, $Bi_aSn_bO_x$, $Bi_aZn_bO_x$, $Ca_aSn_bO_x$, $Ca_aZn_bO_x$, $Cd_aSn_bO_x$, $Cd_aZn_bO_x$, $Ce_aFe_bO_x$, $Ce_aNb_bO_x$, $Ce_aTi_bO_x$, $Ce_aV_bO_x$, $Co_aCu_bO_x$, $Co_aGe_bO_x$, $Co_aLa_bO_x$, $Co_aMg_bO_x$, $Co_aNb_bO_x$, $Co_aPb_bO_x$, $Co_aSn_bO_x$, $Co_aV_bO_x$, $Co_aW_bO_x$, $Co_aZn_bO_x$, $Cr_aCu_bO_x$, $Cr_aLa_bO_x$, $Cr_aMn_bO_x$, $Cr_aNi_bO_x$, $Cr_aSi_bO_x$, $Cr_aTi_bO_x$, $Cr_aY_bO_x$, $Cr_aZn_bO_x$, $Cu_aFe_bO_x$, $Cu_aGa_bO_x$, $Cu_aLa_bO_x$, $Cu_aNa_bO_x$, $Cu_aNi_bO_x$, $Cu_aPb_bO_x$, $Cu_aSn_bO_x$, $Cu_aSr_bO_x$, $Cu_aTi_bO_x$, $Cu_aZn_bO_x$, $Cu_aZr_bO_x$, $Fe_aGa_bO_x$, $Fe_aLa_bO_x$, $Fe_aMo_bO_x$, $Fe_aNb_bO_x$, $Fe_aNi_bO_x$, $Fe_aSn_bO_x$, $Fe_aTi_bO_x$, $Fe_aW_bO_x$, $Fe_aZn_bO_x$, $Fe_aZr_bO_x$, $Ga_aLa_bO_x$, $Ga_aSn_bO_x$, $Ge_aNb_bO_x$, $Ge_aTi_bO_x$, $In_aSn_bO_x$, $K_aNb_bO_x$, $Mn_aNb_bO_x$, $Mn_aSn_bO_x$, $Mn_aTi_bO_x$, $Mn_aY_bO_x$, $Mn_aZn_bO_x$, $Mo_aPb_bO_x$, $Mo_aRb_bO_x$, $Mo_aSn_bO_x$, $Mo_aTi_bO_x$, $Mo_aZn_bO_x$, $Nb_aNi_bO_x$, $Nb_aNi_bO_x$, $Nb_aSr_bO_x$, $Nb_aTi_bO_x$, $Nb_aW_bO_x$, $Nb_aZr_bO_x$, $Ni_aSi_bO_x$, $Ni_aSn_bO_x$, $Ni_aY_bO_x$, $Ni_aZn_bO_x$, $Ni_aZr_bO_x$, $Pb_aSn_bO_x$, $Pb_aZn_bO_x$, $Rb_aW_bO_x$, $Ru_aSn_bO_x$, $Ru_aW_bO_x$, $Ru_aZn_bO_x$, $Sb_aSn_bO_x$, $Sb_aZn_bO_x$, $Sc_aZr_bO_x$, $Si_aSn_bO_x$, $Si_aTi_bO_x$, $Si_aW_bO_x$, $Si_aZn_bO_x$, $Sn_aTa_bO_x$, $Sn_aTi_bO_x$, $Sn_aW_bO_x$, $Sn_aZn_bO_x$, $Sn_aZr_bO_x$, $Sr_aTi_bO_x$, $Ta_aTi_bO_x$, $Ta_aZn_bO_x$, $Ta_aZr_bO_x$, $Ti_aV_bO_x$, $Ti_aW_bO_x$, $Ti_aZn_bO_x$, $Ti_aZr_bO_x$, $V_aZn_bO_x$, $V_aZr_bO_x$, $W_aZn_bO_x$, $W_aZr_bO_x$, $Y_aZr_bO_x$, $Zn_aZr_bO_x$, $Al_aNi_bO_x$ with frit additive, $Cr_aTi_bO_x$ with frit additive, $Fe_aLa_bO_x$ with frit additive, $Fe_aNi_bO_x$ with frit additive, $Fe_aTi_bO_x$ with frit additive, $Nb_aTi_bO_x$ with frit additive, $Nb_aW_bO_x$ with frit additive, $Ni_aZn_bO_x$ with frit additive, $Ni_aZr_bO_x$ with frit additive, $Sb_aSn_bO_x$ with frit additive, $Ta_aTi_bO_x$ with frit additive, or $Ti_aZn_bO_x$ with frit additive; and/or $M^1_aM^2_bM^3_cO_x$ is $Al_aMg_bZn_cO_x$, $Al_aSi_bV_cO_x$, $Ba_aCu_bTi_cO_x$, $Ca_aCe_bZr_cO_x$, $Co_aNi_bTi_cO_x$, $Co_aNi_bZr_cO_x$, $Co_aPb_bSn_cO_x$, $Co_aPb_bZn_cO_x$, $Cr_aSr_bTi_cO_x$, $Cu_aFe_bMn_cO_x$, $Cu_aLa_bSr_cO_x$, $Fe_aNb_bTi_cO_x$, $Fe_aPb_bZn_cO_x$, $Fe_aSr_bTi_cO_x$, $Fe_aTa_bTi_cO_x$, $Fe_aW_bZr_cO_x$, $Ga_aTi_bZn_cO_x$, $La_aMn_bNa_cO_x$, $La_aMn_bSr_cO_x$, $Mn_aSr_bTi_cO_x$, $Mo_aPb_bZn_cO_x$, $Nb_aSr_bTi_cO_x$, $Nb_aSr_bW_cO_x$, $Nb_aTi_bZn_cO_x$, $Ni_aSr_bTi_cO_x$, $Sn_aW_bZn_cO_x$, $Sr_aTi_bV_cO_x$, $Sr_aTi_bZn_cO_x$, or $Ti_aW_bZr_cO_x$.

In certain other preferred embodiments, the metal oxide materials may include those that are in an array of first and second chemo/electro-active materials, wherein the chemo/electro-active materials are selected from the pairings in the group consisting of (i) the first material is $M^1O_x$, and the second material is $M^1_aM^2_bO_x$;

(ii) the first material is $M^1O_x$, and the second material is $M^1_aM^2_bM^3_cO_x$;

(iii) the first material is $M^1_aM^2_bO_x$, and the second material is $M^1_aM^2_bM^3_cO_x$;

(iv) the first material is a first $M^1O_x$, and the second material is a second $M^1O_x$;

(v) the first material is a first $M^1_aM^2_bO_x$, and the second material is a second $M^1_aM^2_bO_x$; and (vi) the first material is a first $M^1_aM^2_bM^3_cO_x$, and the second material is a second $M^1_aM^2_bM^3_cO_x$;

wherein $M^1$ is selected from the group consisting of Ce, Co, Cu, Fe, Ga, Nb, Ni, Pr, Ru, Sn, Ti, Tm, W, Yb, Zn, and Zr;

$M^2$ and $M^3$ are each independently selected from the group consisting of Al, Ba, Bi, Ca, Cd, Ce, Co, Cr, Cu, Fe, Ga, Ge, In, K, La, Mg, Mn, Mo, Na, Nb, Ni, Pb, Pr, Rb, Ru, Sb, Sc, Si, Sn, Sr, Ta, Ti, Tm, V, W, Y, Yb, Zn, and Zr; but $M^1$ and $M^2$ are not the same in $M^1_aM^2_bO_x$, and $M^1$, $M^2$ and $M^3$ are not the same in $M^1_aM^2_bM^3_cO_x$;

a, b and c are each independently about 0.0005 to about 1; and x is a number sufficient so that the oxygen present balances the charges of the other elements present in the chemo/electro-active material.

In certain other preferred embodiments, an array of two or more chemo/electro-active materials may be selected from the group consisting of (i) the chemo/electro-active materials that include $M^1O_x$, (ii) the chemo/electro-active materials that include $M^1_aM^2_bO_x$, and (iii) the chemo/electro-active materials that include $M^1_aM^2_bM^3_cO_x$;

wherein $M^1$ is selected from the group consisting of Al, Ce, Cr, Cu, Fe, Ga, Mn, Nb, Ni, Pr, Sb, Sn, Ta, Ti, W and Zn;

wherein $M^2$ and $M^3$ are each independently selected from the group consisting of Ga, La, Mn, Ni, Sn, Sr, Ti, W, Y, Zn;

wherein $M^1$ and $M^2$ are each different in $M^1_aM^2_bO_x$, and $M^1$, $M^2$ and $M^3$ are each different in $M^1_aM^2_bM^3_cO_x$;

wherein a, b and c are each independently about 0.0005 to about 1; and wherein x is a number sufficient so that the oxygen present balances the charges of the other elements in the chemo/electro-active material.

$M^1$ may for example be selected from the group consisting of Al, Cr, Fe, Ga, Mn, Nb, Ni, Sb, Sn, Ta, Ti and Zn, or from the group consisting of Ga, Nb, Ni, Sb, Sn, Ta, Ti and Zn. $M^2$, $M^3$, or $M^2$ and $M^3$ may be selected from the group consisting of La, Ni, Sn, Ti and Zn, or the group consisting of Sn, Ti and Zn.

The array may contain other numbers of chemo/electro-active materials such as four or eight, and the array may contain at least one chemo/electro-active material that comprises $M^1O_x$, and at least three chemo/electro-active materials that each comprise $M^1_aM^2_bO_x$. Alternatively, the array may contain (i) at least one chemo/electro-active material that comprises $M^1O_x$, and at least four chemo/electro-active materials that each comprise $M^1_aM^2_bO_x$; or (ii) at least two chemo/electro-active materials that each comprise $M^1O_x$, and at least four chemo/electro-active materials that each comprise $M^1_aM^2_bO_x$; or (iii) at least three chemo/electro-active materials that each comprise $M^1_aM^2_bO_x$, and at least one chemo/electro-active material that comprises $M^1_aM^2_bM^3_cO_x$.

Chemo/electro-active materials useful in the apparatus of this invention may be selected from one or more members of the group consisting of a chemo/electro-active material that comprises $Al_aNi_bO_x$ a chemo/electro-active material that comprises $CeO_2$, a chemo/electro-active material that comprises $Cr_aMn_bO_x$, a chemo/electro-active material that comprises $Cr_aTi_bO_x$ a chemo/electro-active material that comprises $Cr_aY_bO_x$ a chemo/electro-active material that comprises $Cu_aGa_bO_x$, a chemo/electro-active material that comprises $Cu_aLa_bO_x$ a chemo/electro-active material that comprises CuO, a chemo/electro-active material that comprises $Fe_aLa_bO_x$ a chemo/electro-active material that comprises $Fe_aNi_bO_x$ a chemo/electro-active material that comprises $Fe_aTi_bO_x$ a chemo/electro-active material that comprises $Ga_aTi_bZn_cO_x$ a chemo/electro-active material that comprises $Mn_aTi_bO_x$ a chemo/electro-active material that comprises $Nb_aSr_bO_x$, a chemo/electro-active material that comprises $Nb_aTi_bO_x$ a chemo/electro-active material that comprises $Nb_aTi_bZn_cO_x$ a chemo/electro-active material that comprises $Nb_aW_bO_x$ a chemo/electro-active material that comprises NiO, a chemo/electro-active material that comprises $Ni_aZn_bO_x$ a chemo/electro-active material that comprises $Pr_6O_{11}$, a chemo/electro-active material that comprises $Sb_aSn_bO_x$.

a chemo/electro-active material that comprises $SnO_2$, a chemo/electro-active material that comprises $Ta_aTi_bO_x$, and a chemo/electro-active material that comprises $Ti_aZn_bO_x$.

a chemo/electro-active material that comprises $WO_3$, and a chemo/electro-active material that comprises ZnO.

wherein a, b and c are each independently about 0.0005 to about 1; and wherein x is a number sufficient so that the oxygen present balances the charges of the other elements in the chemo/electro-active material.

Chemo/electro-active materials useful in this invention may also be selected from subgroups of the foregoing formed by omitting any one or more members from the whole group as set forth in the list above. As a result, the chemo/electro-active materials in such instance may not only be any one or more member(s) selected from any subgroup of any size that may be formed from the whole group as set forth in the list above, but the subgroup may also exclude the members that have been omitted from the whole group to form the subgroup. The subgroup formed by omitting various members from the whole group in the list above may, moreover, contain any number of the members of the whole group such that those members of the whole group that are excluded to form the subgroup are absent from the subgroup. Representative subgroups are set forth below.

For example, of the above, one or more members of the group consisting of
- a chemo/electro-active material that comprises $CeO_2$,
- a chemo/electro-active material that comprises $SnO_2$,
- a chemo/electro-active material that comprises ZnO
- a chemo/electro-active material that comprises $Al_aNi_bO_x$
- a chemo/electro-active material that comprises $Cr_aTi_bO_x$
- a chemo/electro-active material that comprises $Cu_aLa_bO_x$
- a chemo/electro-active material that comprises $Fe_aLa_bO_x$
- a chemo/electro-active material that comprises $Fe_aNi_bO_x$
- a chemo/electro-active material that comprises $Fe_aTi_bO_x$
- a chemo/electro-active material that comprises $Ga_aTi_bZn_cO_x$
- a chemo/electro-active material that comprises $Nb_aTi_bO_x$
- a chemo/electro-active material that comprises $Nb_aTi_bZn_cO_x$
- a chemo/electro-active material that comprises $Nb_aW_bO_x$
- a chemo/electro-active material that comprises $Ni_aZn_bO_x$
- a chemo/electro-active material that comprises $Sb_aSn_bO_x$
- a chemo/electro-active material that comprises $Ta_aTi_bO_x$, and
- a chemo/electro-active material that comprises $Ti_aZn_bO_x$ may contain a frit additive.

In the apparatus of this invention, a chemo/electro-active material that comprises $M^1{}_aM^2{}_bO_x$ may be selected from the group consisting of
- a chemo/electro-active material that comprises $Al_aNi_bO_x$
- a chemo/electro-active material that comprises $Cr_aTi_bO_x$, and
- a chemo/electro-active material that comprises $Fe_aLa_bO_x$.

or the group consisting of
- a chemo/electro-active material that comprises $Cr_aTi_bO_x$
- a chemo/electro-active material that comprises $Fe_aLa_bO_x$, and
- a chemo/electro-active material that comprises $Fe_aNi_bO_x$ or the group consisting of
- a chemo/electro-active material that comprises $Fe_aLa_bO_x$
- a chemo/electro-active material that comprises $Fe_aNi_bO_x$, and
- a chemo/electro-active material that comprises $Ni_aZn_bO_x$ or the group consisting of
- a chemo/electro-active material that comprises $Fe_aNi_bO_x$
- a chemo/electro-active material that comprises $Ni_aZn_bO_x$, and
- a chemo/electro-active material that comprises $Sb_aSn_bO_x$.

or the group consisting of
- a chemo/electro-active material that comprises $Al_aNi_bO_x$
- a chemo/electro-active material that comprises $Cr_aTi_bO_x$
- a chemo/electro-active material that comprises $Fe_aLa_bO_x$
- a chemo/electro-active material that comprises $Fe_aNi_bO_x$
- a chemo/electro-active material that comprises $Ni_aZn_bO_x$, and
- a chemo/electro-active material that comprises $Sb_aSn_bO_x$.

or the group consisting of
- a chemo/electro-active material that comprises $Al_aNi_bO_x$
- a chemo/electro-active material that comprises $Cr_aTi_bO_x$, and
- a chemo/electro-active material that comprises $Mn_aTi_bO_x$ or the group consisting of
- a chemo/electro-active material that comprises $Nb_aTi_bO_x$
- a chemo/electro-active material that comprises $Ni_aZn_bO_x$, and
- a chemo/electro-active material that comprises $Sb_aSn_bO_x$ or the group consisting of
- a chemo/electro-active material that comprises $Ni_aZn_bO_x$
- a chemo/electro-active material that comprises $Sb_aSn_bO_x$, and
- a chemo/electro-active material that comprises $Ta_aTi_bO_x$ or the group consisting of
- a chemo/electro-active material that comprises $Sb_aSn_bO_x$
- a chemo/electro-active material that comprises $Ta_aTi_bO_x$, and
- a chemo/electro-active material that comprises $Ti_aZn_bO_x$.

or the group consisting of
- a chemo/electro-active material that comprises $Cr_aMn_bO_x$
- a chemo/electro-active material that comprises $Cr_aTi_bO_x$, and
- a chemo/electro-active material that comprises $Cr_aY_bO_x$ or the group consisting of
- a chemo/electro-active material that comprises $Cr_aTi_bO_x$
- a chemo/electro-active material that comprises $Cr_aY_bO_x$, and
- a chemo/electro-active material that comprises $Cu_aGa_bO_x$ or the group consisting of
- a chemo/electro-active material that comprises $Cr_aY_bO_x$
- a chemo/electro-active material that comprises $Cu_aGa_bO_x$, and
- a chemo/electro-active material that comprises $Cu_aLa_bO_x$ or the group consisting of
- a chemo/electro-active material that comprises $Cu_aGa_bO_x$
- a chemo/electro-active material that comprises $Cu_aLa_bO_x$, and
- a chemo/electro-active material that comprises $Fe_aLa_bO_x$.

or the group consisting of
- a chemo/electro-active material that comprises $Cr_aMn_bO_x$
- a chemo/electro-active material that comprises $Cr_aTi_bO_x$
- a chemo/electro-active material that comprises $Cr_aY_bO_x$
- a chemo/electro-active material that comprises $Cu_aGa_bO_x$
- a chemo/electro-active material that comprises $Cu_aLa_bO_x$, and
- a chemo/electro-active material that comprises $Fe_aLa_bO_x$.

or the group consisting of
- a chemo/electro-active material that comprises $Cr_aY_bO_x$
- a chemo/electro-active material that comprises $Cu_aGa_bO_x$, and
- a chemo/electro-active material that comprises $Cu_aLa_bO_x$ or the group consisting of
- a chemo/electro-active material that comprises $Cu_aGa_bO_x$,
- a chemo/electro-active material that comprises $Cu_aLa_bO_x$, and
- a chemo/electro-active material that comprises $Fe_aTi_bO_x$ or the group consisting of
- a chemo/electro-active material that comprises $Cr_aMn_bO_x$
- a chemo/electro-active material that comprises $Mn_aTi_bO_x$, and
- a chemo/electro-active material that comprises $Nb_aSr_bO_x$ In the apparatus of this invention, a chemo/electro-active material that comprises $M^1{}_aM^2{}_bO_x$, or a chemo/electro-active material that comprises $M^1{}_aM^2{}_bM^3{}_cO_x$, may be selected from the group consisting of
  a chemo/electro-active material that comprises $Cr_aTi_bO_x$,
  a chemo/electro-active material that comprises $Mn_aTi_bO_x$, and
  a chemo/electro-active material that comprises $Nb_aTi_bZn_cO_x$ or the group consisting of
  a chemo/electro-active material that comprises $Mn_aTi_bO_x$
  a chemo/electro-active material that comprises $Nb_aTi_bZn_cO_x$, and
  a chemo/electro-active material that comprises $Ta_aTi_bO_x$ or the group consisting of
  a chemo/electro-active material that comprises $Nb_aTi_bZn_cO_x$
  a chemo/electro-active material that comprises $Ta_aTi_bO_x$, and
  a chemo/electro-active material that comprises $Ti_aZn_bO_x$.

or the group consisting of
  a chemo/electro-active material that comprises $Al_aNi_bO_x$
  a chemo/electro-active material that comprises $Cr_aTi_bO_x$
  a chemo/electro-active material that comprises $Mn_aTi_bO_x$
  a chemo/electro-active material that comprises $Nb_aTi_bZn_cO_x$
  a chemo/electro-active material that comprises $Ta_aTi_bO_x$, and
  a chemo/electro-active material that comprises $Ti_aZn_bO_x$.

or the group consisting of
  a chemo/electro-active material that comprises $Ga_aTi_bZn_cO_x$
  a chemo/electro-active material that comprises $Nb_aTi_bO_x$, and
  a chemo/electro-active material that comprises $Ni_aZn_bO_x$ or the group consisting of
  a chemo/electro-active material that comprises $Ga_aTi_bZn_bO_x$
  a chemo/electro-active material that comprises $Nb_aTi_bO_x$
  a chemo/electro-active material that comprises $Ni_aZn_bO_x$
  a chemo/electro-active material that comprises $Sb_aSn_bO_x$
  a chemo/electro-active material that comprises $Ta_aTi_bO_x$, and
  a chemo/electro-active material that comprises $Ti_aZn_bO_x$.

or the group consisting of
  a chemo/electro-active material that comprises $Cu_aLa_bO_x$
  a chemo/electro-active material that comprises $Fe_aTi_bO_x$, and
  a chemo/electro-active material that comprises $Ga_aTi_bZn_cO_x$ or the group consisting of
  a chemo/electro-active material that comprises $Fe_aTi_bO_x$
  a chemo/electro-active material that comprises $Ga_aTi_cZn_bO_x$, and
  a chemo/electro-active material that comprises $Nb_aW_bO_x$.

or the group consisting of
  a chemo/electro-active material that comprises $Cr_aY_bO_x$
  a chemo/electro-active material that comprises $Cu_aGa_bO_x$,
  a chemo/electro-active material that comprises $Cu_aLa_bO_x$
  a chemo/electro-active material that comprises $Fe_aTi_bO_x$
  a chemo/electro-active material that comprises $Ga_aTi_bZn_cO_x$, and
  a chemo/electro-active material that comprises $Nb_aW_bO_x$.

or the group consisting of
  a chemo/electro-active material that comprises $Mn_aTi_bO_x$
  a chemo/electro-active material that comprises $Nb_aSr_bO_x$, and
  a chemo/electro-active material that comprises $N_bTi_bZn_cO_x$ In the apparatus of this invention, a chemo/electro-active material that comprises $M^1O_x$, a chemo/electro-active material that comprises $M^1{}_aM^2{}_bO_x$, or a chemo/electro-active material that comprises $M^1{}_aM^2{}_bM^3{}_cO_x$, may be selected from the group consisting of
  a chemo/electro-active material that comprises $Ga_aTi_bZn_cO_x$
  a chemo/electro-active material that comprises $Nb_aTi_bO_x$
  a chemo/electro-active material that comprises $Ni_aZn_bO_x$, and
  a chemo/electro-active material that comprises $SnO_2$ or the group consisting of
  a chemo/electro-active material that comprises $Ga_aTi_bZn_cO_x$
  a chemo/electro-active material that comprises $Nb_aTi_bO_x$
  a chemo/electro-active material that comprises $Ni_aZn_bO_x$
  a chemo/electro-active material that comprises $SnO_2$,
  a chemo/electro-active material that comprises $Ta_aTi_bO_x$, and
  a chemo/electro-active material that comprises $Ti_aZn_bO_x$.

or the group consisting of
  a chemo/electro-active material that comprises $Nb_aSr_bO_x$
  a chemo/electro-active material that comprises $Nb_aTi_bZn_cO_x$, and
  a chemo/electro-active material that comprises $Pr_6O_{11}$ or the group consisting of
  a chemo/electro-active material that comprises $Nb_aTi_bZn_cO_x$
  a chemo/electro-active material that comprises $Pr_6O_{11}$, and
  a chemo/electro-active material that comprises $Ti_aZn_bO_x$.

or the group consisting of
  a chemo/electro-active material that comprises $Cr_aMn_bO_x$
  a chemo/electro-active material that comprises $Mn_aTi_bO_x$
  a chemo/electro-active material that comprises $Nb_aSr_bO_x$
  a chemo/electro-active material that comprises $Nb_aTi_cZn_bO_x$
  a chemo/electro-active material that comprises $Pr_6O_{11}$, and
  a chemo/electro-active material that comprises $Ti_aZn_bO_x$.

In the apparatus of this invention, a chemo/electro-active material that comprises $M^1O_x$, or a chemo/electro-active material that comprises $M^1{}_aM^2{}_bO_x$ may be selected from the group consisting of
  a chemo/electro-active material that comprises $Nb_aTi_bO_x$
  a chemo/electro-active material that comprises $Ni_aZn_bO_x$, and
  a chemo/electro-active material that comprises $SnO_2$.

or the group consisting of
  a chemo/electro-active material that comprises $Ni_aZn_bO_x$
  a chemo/electro-active material that comprises $SnO_2$, and
  a chemo/electro-active material that comprises $Ta_aTi_bO_x$ or the group consisting of
  a chemo/electro-active material that comprises $SnO_2$,
  a chemo/electro-active material that comprises $Ta_aTi_bO_x$, and
  a chemo/electro-active material that comprises $Ti_aZn_bO_x$.

or the group consisting of
   a chemo/electro-active material that comprises $Nb_aTi_bO_x$
   a chemo/electro-active material that comprises $Ni_aZn_bO_x$
   a chemo/electro-active material that comprises $Sb_aSn_bO_x$, and
   a chemo/electro-active material that comprises ZnO.

or the group consisting of
   a chemo/electro-active material that comprises $Ni_aZn_bO_x$
   a chemo/electro-active material that comprises $Sb_aSn_bO_x$
   a chemo/electro-active material that comprises $Ta_aTi_bO_x$, and
   a chemo/electro-active material that comprises ZnO or the group consisting of
   a chemo/electro-active material that comprises $Sb_aSn_bO_x$
   a chemo/electro-active material that comprises $Ta_aTi_bO_x$
   a chemo/electro-active material that comprises $Ti_aZn_bO_x$, and
   a chemo/electro-active material that comprises ZnO or the group consisting of
   a chemo/electro-active material that comprises $Ta_aTi_bO_x$
   a chemo/electro-active material that comprises $Ti_aZn_bO_x$, and
   a chemo/electro-active material that comprises ZnO.

or the group consisting of
   a chemo/electro-active material that comprises $Nb_aTi_bO_x$
   a chemo/electro-active material that comprises $Ni_aZn_bO_x$
   a chemo/electro-active material that comprises $Sb_aSn_bO_x$
   a chemo/electro-active material that comprises $Ta_aTi_bO_x$
   a chemo/electro-active material that comprises $Ti_aZn_bO_x$, and
   a chemo/electro-active material that comprises ZnO.

or the group consisting of
   a chemo/electro-active material that comprises $Al_aNi_bO_x$
   a chemo/electro-active material that comprises $Cr_aMn_bO_x$, and
   a chemo/electro-active material that comprises CuO or the group consisting of
   a chemo/electro-active material that comprises $Cr_aMn_bO_x$
   a chemo/electro-active material that comprises CuO, and
   a chemo/electro-active material that comprises $Nb_aSr_bO_x$ or group consisting of
   a chemo/electro-active material that comprises CuO
   a chemo/electro-active material that comprises $Nb_aSr_bO_x$, and
   a chemo/electro-active material that comprises $Pr_6O_{11}$ or group consisting of
   a chemo/electro-active material that comprises $Nb_aSr_bO_x$
   a chemo/electro-active material that comprises $Pr_6O_{11}$, and
   a chemo/electro-active material that comprises $WO_3$.

or group consisting of
   a chemo/electro-active material that comprises $Al_aNi_bO_x$
   a chemo/electro-active material that comprises $Cr_aMn_bO_x$
   a chemo/electro-active material that comprises CuO
   a chemo/electro-active material that comprises $Nb_aSr_bO_x$
   a chemo/electro-active material that comprises $Pr_6O_{11}$, and
   a chemo/electro-active material that comprises $WO_3$.

Any method of depositing the chemo/electro-active material to a substrate is suitable. One technique used for deposition is applying a semiconducting material on an alumina substrate on which electrodes are screen printed. The semiconducting material can be deposited on top of electrodes by hand painting semiconducting materials onto the substrate, pipetting materials into wells, thin film deposition, or thick film printing techniques. Most techniques are followed by a final firing to sinter the semiconducting materials.

Figure 2:
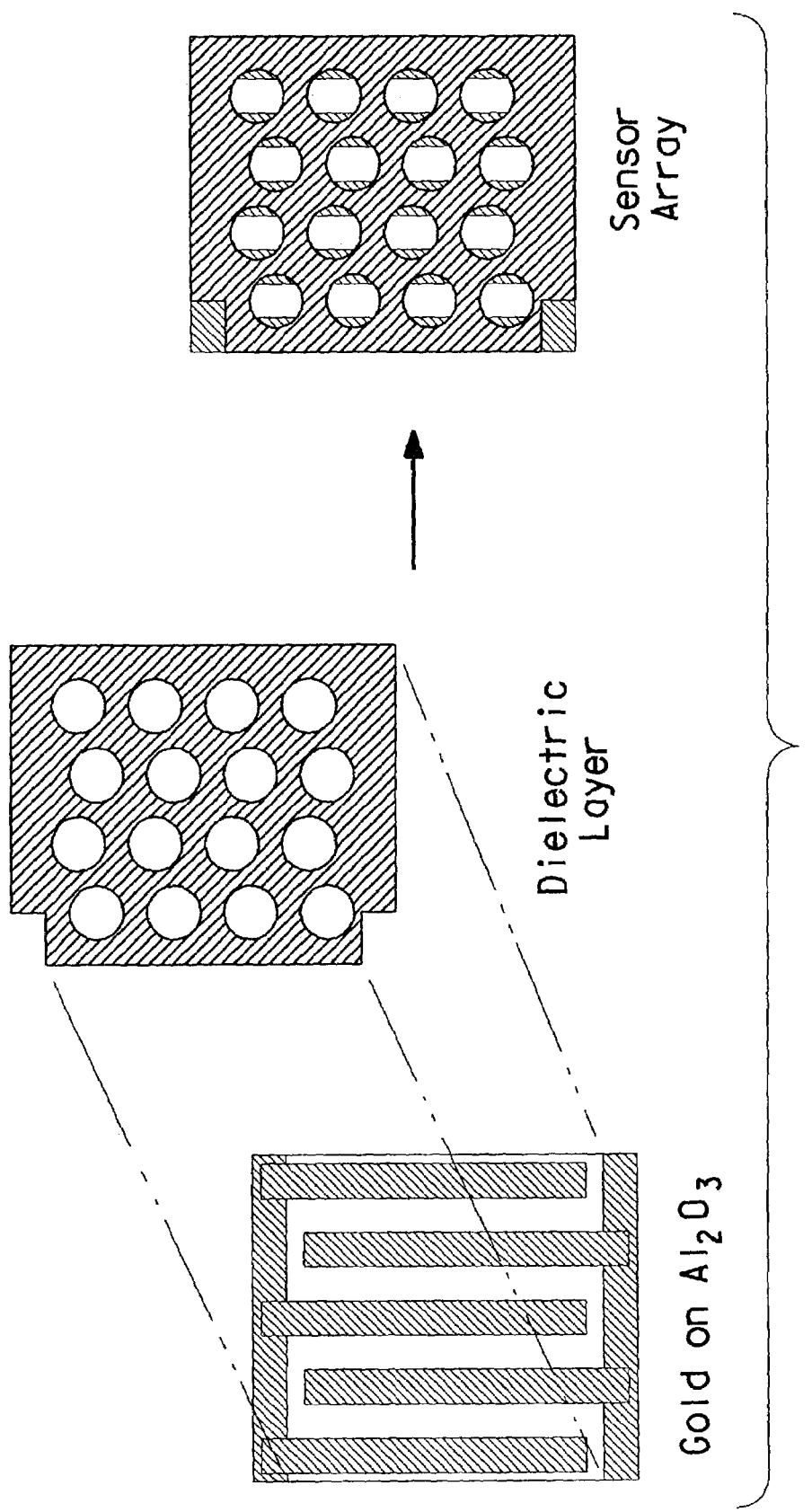
FIG. 2 is a schematic of the pattern of interdigitated electrodes overlaid with a dielectric overlayer, forming sixteen blank wells, in an array of chemo/electro-active materials.
Figure 3A:
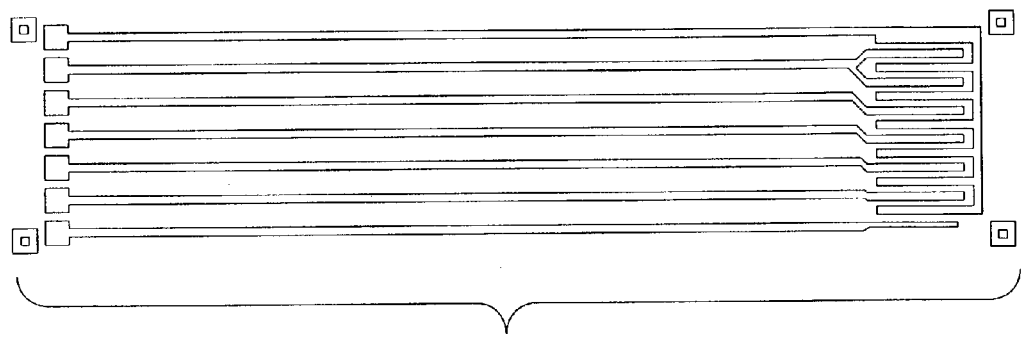
FIG. 3 depicts the electrode pattern, dielectric pattern, and sensor material pattern in an array of chemo/electro-active materials.
Figure 3B:
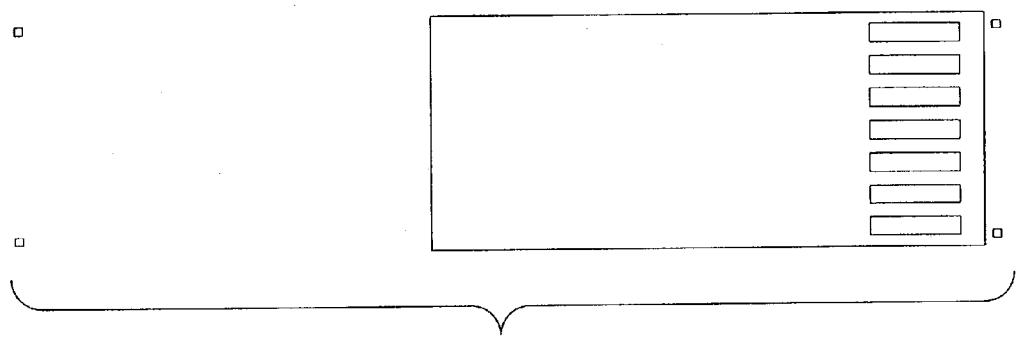
Figure 3C:
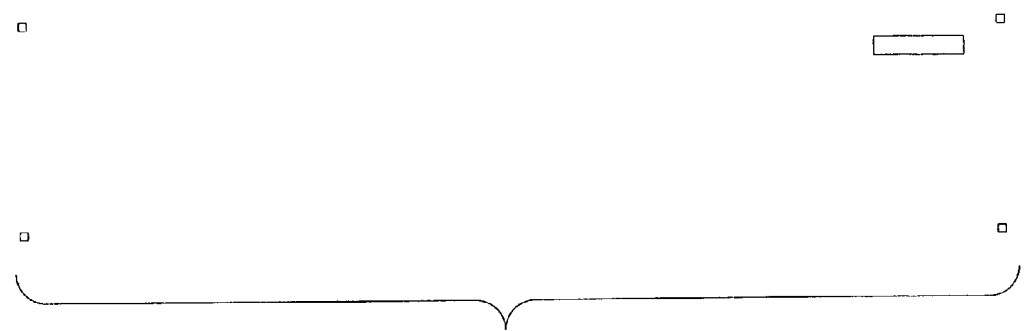
Figure 4:
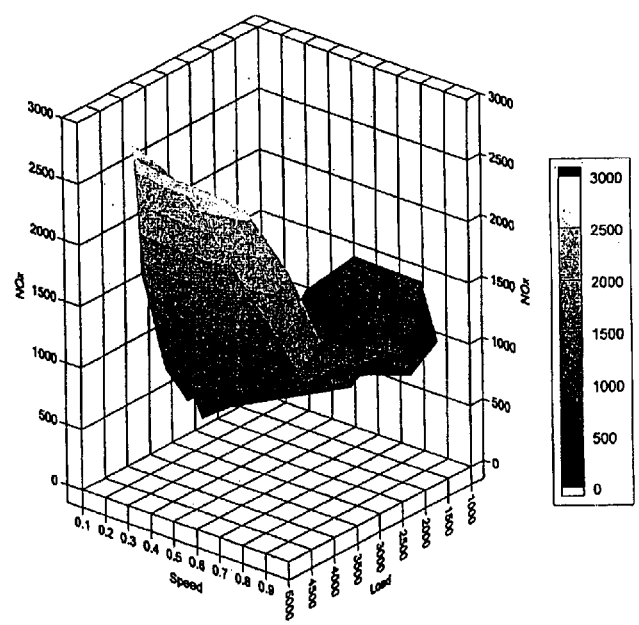
FIG. 4 is an illustration of a map that relates speed to load to measurements concerning the presence of nitrogen oxides ($NO_x$).

Techniques for screen-printing substrates with the electrodes and chemo/electro-active materials are illustrated in FIGS. 2–3. FIG. 2 depicts a method of using interdigitated electrodes overlaid with dielectric material, forming blank wells into which the chemo/electro-active materials can be deposited. FIG. 3 depicts an electrode screen pattern for an array of 6 materials which is printed on both sides of the substrate to provide for a 12-material array chip. Two of the electrodes are in parallel so it holds only 6 unique materials. Counting down from the top of the array shown in FIG. 3, the top two materials can only be accessed simultaneously by the split electrode with which they have shared contact. Below that is the screen pattern for the dielectric material, which is screen printed on top of the electrodes on both sides of the substrate to prevent the material from being fouled by contact with the gas mixture, such as a deposit of soot that could reduce the sensitivity of a sensor material to a gas or cause a short. Below that is the screen pattern for the actual sensor materials. This is printed in the holes in the dielectric on top of the electrodes. When more than one material is used in the array, the individual materials are printed one at a time.

The geometry of a sensor material as fabricated in an array, including such characteristics as its thickness, selection of a compound or composition for use as the sensor, and the voltage applied across the array, can vary depending on the sensitivity required. If desired, the apparatus may be constructed in a size such that it may be passed through an opening that is the size of a circle having a diameter of no more than about 150 mm, or no more than about 100 mm, or no more than about 50 mm, or no more than about 25 mm, or no more than about 18 mm, as the requirements of it usage may dictate. The sensor materials are preferably connected in parallel in a circuit to which a voltage of about 1 to about 20, preferably about 1 to about 12, volts is applied across the sensor materials.

As noted, the types of electrical response characteristics that may be measured include AC impedance or resistance, capacitance, voltage, current or DC resistance. It is preferred to use resistance as the electric response characteristic of a sensor material that is measured to perform analysis of a gas mixture and/or a component therein. For example, a suitable sensor material may be that which, when at a temperature of about 400° C. or above, has a resistivity of at least about 1 ohm-cm, and preferably at least about 10 ohm-cm, and yet no more than about $10^6$ ohm-cm, preferably no more than about $10^5$ ohm-cm, and more preferably no more than about $10^4$ ohm-cm. Such a sensor material may also be characterized as that which exhibits, preferably at a temperature of about 400° C. or above, upon exposure to a gas mixture, a change in resistance of at least about 0.1 percent, and preferably at least about 1 percent, as compared to the resistance in the absence of exposure. When using such materials, it is possible if desired to generate a signal that is proportional to the resistance exhibited by any one or more of the chemo/electro-active materials upon exposure to a gas mixture of interest.

Regardless of the type of response characteristic that is measured for the purpose of analyzing a mixture and/or a gaseous component of interest therein, it is desirable that a sensor material be utilized for which a quantified value of that response characteristic is stable over an extended period of time. When the sensor material is exposed to a mixture containing the analyte, the concentration of the analyte being a function of the composition of the particular gas mixture in which it is contained, the value of the response of the sensor material will preferably remain constant or vary to only a small extent during exposure to the mixture over an extended period of time at a constant temperature. For example, the value of the response, if it varies, will vary by no more than about twenty percent, preferably no more than about ten percent, more preferably no more than about five percent, and most preferably no more than about one percent over a period of at least about 1 minute, or preferably a period of hours such as at least about 1 hour, preferably at least about 10 hours, more preferably at least about 100 hours, and most preferably at least about 1000 hours. One of the advantages of the types of sensor materials described above is that they are characterized by this kind of stability of response.

An electrical response is determined for each chemo/electro-active material upon exposure of the array to a gas mixture, and means for determining the response include conductors interconnecting the sensor materials. The conductors are in turn connected to electrical input and output circuitry, including data acquisition and manipulation devices as appropriate to measure and record a response exhibited by a sensor material in the form of an electrical signal. The value of a response, such as a measurement related to resistance, may be indicated by the size of the signal. One or more signals may be generated by an array of sensors as to each analyte component in the mixture, whether the analyte is one or more individual gases and/or one or more subgroups of gases.

An electrical response is determined for each individual chemo/electro-active material separately from that of each of the other chemo/electro-active materials. This can be accomplished by accessing each chemo/electro-active material with an electric current sequentially, using a multiplexer to provide signals differentiated between one material and another in, for example, the time domain or frequency domain. It is consequently preferred that no chemo/electro-active material be joined in a series circuit with any other such material. One electrode, by which a current is passed to a chemo/electro-active material, can nevertheless be laid out to have contact with more than one material. An electrode may have contact with all, or fewer than all, of the chemo/electro-active materials in an array. For example, if an array has 12 chemo/electro-active materials, an electrode may have contact with each member of a group of 2, 3, 4, 5 or 6 (or, optionally, more in each instance) of the chemo/electro-active materials. The electrode will preferably be laid out to permit an electrical current to be passed to each member of such group of chemo/electro-active materials sequentially.

A conductor such as a printed circuit may be used to connect a voltage source to a sensor material, and, when a voltage is applied across the sensor material, a corresponding current is created through the material. Although the voltage may be AC or DC, the magnitude of the voltage will typically be held constant. The resulting current is proportional to both the applied voltage and the resistance of the sensor material. A response of the material in the form of either the current, voltage or resistance may be determined, and means for doing so include commercial analog circuit components such as precision resistors, filtering capacitors and operational amplifiers (such as a OPA4340). As voltage, current and resistance is each a known function of the other two electrical properties, a known quantity for one property may be readily converted to that of another.

Resistance may be determined, for example, in connection with the digitization of an electrical response. Means for digitizing an electrical response include an analog to digital (A/D) converter, as known in the art, and may include, for example, electrical components and circuitry that involve the operation of a comparator. An electrical response in the form of a voltage signal, derived as described above as a result of applying a voltage across a sensor material, is used as an input to a comparator section (such as a LM339). The other input to the comparator is driven by a linear ramp produced by charging a capacitor using a constant current source configured from an operational amplifier (such as a LT1014) and an external transistor (such as a PN2007a). The ramp is controlled and monitored by a microcomputer (such as a T89C51CC01). A second comparator section is also driven by the ramp voltage, but is compared to a precise reference voltage. The microcomputer captures the length of time from the start of the ramp to the activation of the comparators to generate a signal based on the counted time.

The resistance of the sensor material is then calculated, or quantified as a value, by the microcomputer from the ratio of the time signal derived from the voltage output of the material to a time signal corresponding to a known look-up voltage and, ultimately, to the resistance that is a function of the look-up voltage. A microprocessor chip, such as a T89C51CCO1, can be used for this function. The microprocessor chip may also serve as means for determining a change in the resistance of a sensor material by comparing a resistance, determined as above, to a previously determined value of the resistance.

Electrical properties such as impedance or capacitance may be determined, for example, by the use of circuitry components such as an impedance meter, a capacitance meter or inductance meter.

Means for digitizing the temperature of an array of chemo/electro-active materials can include, for example, components as described above that convert a signal representative of a physical property, state or condition of a temperature measuring device to a signal based on counted time.

In one embodiment, analysis of a multi-component gas mixture is complete upon the generation of an electrical response, such as resistance, in the manner described above. As a measurement of resistance exhibited by a sensor material upon exposure to a gas mixture is a function of the partial pressure within the mixture of one or more component gases, the measured resistance provides useful information about the composition of the gas mixture. The information may, for example, indicate the presence or absence within the mixture of a particular gas or subgroup of gases. In other embodiments, however, it may be preferred to manipulate, or further manipulate, an electrical response in the manner necessary to obtain information related to the concentration within the mixture of one or more particular component gases or subgroups of gases, or to calculate the actual concentration within the mixture of one or more component gases or subgroups.

Means for obtaining information concerning the relative concentration within the mixture of one or more individual component gases and/or one or more subgroups of gases, or for detecting the presence of, or calculating the actual concentration of, one or more individual component gases and/or subgroups within the mixture, may include a modeling algorithm that incorporates either a PLS (Projection onto Latent Systems) model, a back-propagation neural network model, or a combination of the two, along with signal pre-processing and output post-processing. Signal pre-processing includes, but is not limited to, such operations as principle component analyses, simple linear transformations and scaling, logarithmic and natural logarithmic transformations, differences of raw signal values (e.g., resistances), and differences of logarithmic values. The algorithm contains a model whose parameters have been previously determined, and that empirically models the relationship between the pre-processed input signal and information related to the gas concentration of the species of interest. Output post-processing includes, but is not limited to, all of the operations listed above, as well as their inverse operations.

The model is constructed using equations in which constants, coefficients or other factors are derived from predetermined values characteristic of a precisely measured electrical response of an individual sensor material to a particular individual gas or subgroup expected to be present as a component in the mixture to be analyzed. The equations may be constructed in any manner that takes temperature into account as a value separate and apart from the electrical responses exhibited by the sensor materials upon exposure to a gas mixture. Each individual sensor material in the array differs from each of the other sensors in its response to at least one of the component gases or subgroups in the mixture, and these different responses of each of the sensors is determined and used to construct the equations used in the model.

A change of temperature in the array may be indicated by a change in the quantified value of an electrical response characteristic, resistance for example, of a sensor material. At a constant partial pressure in the mixture of a gas of interest, the value of an electrical response characteristic of a sensor material may vary with a change in temperature of the array, and thus the material. This change in the value of an electrical response characteristic may be measured for the purpose of determining or measuring the extent of change of, and thus a value for, temperature. The temperature of the array will be the same, or substantially the same, as the temperature of the gas mixture unless the array is being maintained at a preselected temperature by a heater located in the substrate. If the array is being heated by a heater, the temperature of the array will be substantially in the range within which the heater cycles on and off.

It is not required, but is preferred, that this measurement of temperature be made independently of information related to the compositional content of a gas mixture. This can be done by not using sensors that provide compositional information for the additional purpose of determining temperature, and, optionally, by connecting the temperature measuring device in parallel circuitry with the sensor materials, rather than in series. Means for measuring temperature include a thermocouple or a pyrometer incorporated with an array of sensors. If the termperature determining device is a thermistor, which is typically a material that is not responsive to an analyte gas, the thermistor is preferably made from a different material than the material from which any of the gas sensors is made. Regardless of the method by which temperature or change in temperature is determined, a temperature value or a quantified change in temperature is a desirable input, preferably in digitized form, from which an analysis of a mixture of gases and/or a component therein may be performed.

In the method and apparatus of this invention, unlike various prior-art technologies, there is no need to separate the component gases of a mixture for purposes of performing an analysis, such as by a membrane or electrolytic cell. There is also no need when performing an analysis by means of this invention to employ a reference gas external to the system, such as for the purpose of bringing a response or analytical results back to a base line value. A value representative of a reference state may, however, be used as a factor in an algorithm by which information related to the composition of the gas mixture is determined. With the exception of preliminary testing, during which a standardized response value to be assigned to the exposure of each individual sensor material to each individual analyte gas is determined, the sensor materials are exposed only to the mixture in which an analyte gas and/or subgroup is contained. The sensor materials are not exposed to any other gas to obtain response values for comparison to those obtained from exposure to the mixture containing an analyte. The analysis of the mixture is therefore performed only from the electrical responses obtained upon exposure of the chemo/electro-active materials to the mixture containing the analyte. No information about an analyte gas and/or subgroup is inferred by exposure of the sensor materials to any gas other than the analyte itself as contained within the mixture.

This invention is therefore useful at the higher temperatures found in automotive emission systems, typically in the range of from about 400° C. to about 1000° C. In addition to gasoline and diesel internal combustion engines, however, there is a variety of other combustion processes to which this invention could be applied, including stack or burner emissions of all kinds such as resulting from chemical manufacturing, electrical generation, waste incineration and air heating. These applications require the detection of gases such as nitrogen oxides, ammonia, carbon monoxide, hydrocarbons and oxygen at the ppm to percent levels, typically in a highly corrosive environment.

When the multi-component gas mixture comprises a nitrogen oxide, a hydrocarbon, or both, or any of the other gases mentioned herein, the apparatus may be used to determine the presence and/or concentration of a nitrogen oxide and/or hydrocarbon in the multi-component gas mixture. The apparatus may also be used to determine the presence and/or concentration of any one or more to the other gases mentioned herein that may be present in a multi-component gas mixture. For this purpose, the electrical response, in the apparatus of this invention, of one or more of a chemo/electro-active material that comprises $M^1O_x$, a chemo/electro-active material that comprises $M^1_aM^2_bO_x$, and a chemo/electro-active material that comprises $M^1_aM^2_bM^3_cO_x$, may be related to one or more of the presence of a nitrogen oxide within the gas mixture, the presence of a hydrocarbon within the gas mixture, the collective concentration of all nitrogen oxides within the gas mixture, and the concentration of a hydrocarbon within the gas mixture.

This invention is also useful for detecting and measuring gases in other systems such as those in which odor detection is important, and/or that are at lower temperature, such as in the medical, agricultural or food and beverage industries, or in the ventilation system of a building or a vehicle for transportation. An array of chemo/electro-active materials could be used, for example, to supplement the results of, or calibrate, a gas chromatograph.

This invention therefore provides methods and apparatus for directly sensing the presence and/or concentration of one or more gases in an multi-component gas system, comprising an array of at least two chemo/electro-active materials chosen to detect analyte gases or subgroups of gases in a multi-component gas stream. The multi-component gas system can be at essentially any temperature that is not so low or so high that the sensor materials are degraded or the sensor apparatus otherwise malfunctions. In one embodiment, the gas system may be at a lower temperature such as room temperature (about 25° C.) or elsewhere in the range of about 0° C. to less than about 100° C., whereas in other embodiments the gas mixture may at a higher temperature such as in the range of about 400° C. to about 1000° C. or more. The gas mixture may therefore have a temperature that is about 0° C. or more, about 100° C. or more, about 200° C. or more, about 300° C. or more, about 400° C. or more, about 500° C. or more, about 600° C. or more, about 700° C. or more, or about 800° C. or more, and yet is less than about 1000° C., is less than about 900° C., is less than about 800° C., is less than about 700° C., is less than about 600° C., is less than about 500° C., is less than about 400° C., is less than about 300° C., is less than about 200° C., or is less than about 100° C.

In applications in which the gas mixture is above about 400° C., the temperature of the sensor materials and the array may be determined substantially only, and preferably is determined solely, by the temperature of the gas mixture in which a gaseous analyst is contained. This is typically a variable temperature. When higher-temperature gases are being analyzed, it may be desirable to provide a heater with the array to bring the sensor materials quickly to a minimum temperature. Once the analysis has begun, however, the heater (if used) is typically switched off, and no method is provided to maintain the sensor materials at a preselected temperature. The temperature of the sensor materials thus rises or falls to the same extent that the temperature of the surrounding environment does. The temperature of the surrounding environment, and thus the sensors and the array, is typically determined by (or results from) substantially only the temperature of the gas mixture to which the array is exposed.

In applications in which the gas mixture is below about 400° C., it may be preferred to maintain the sensor materials and the array at a preselected temperature of about 200° C. or above, and preferably 400° C. or above. This preselected temperature may be substantially constant, or preferably is constant. The preselected temperature may also be about 500° C. or above, about 600° C. or above, about 700° C. or above, about 800° C. or above, about 900° C. or above, or about 1000° C. or above. This may be conveniently done with a heater incorporated with the array, in a manner as known in the art. If desired, a separate micro heater means may be supplied for each separate chemo/electro-active material, and any one or more of the materials may be heated to the same or a different temperature. The temperature of the gas mixture in such case may also be below about 300° C., below about 200° C., below about 100° C., or below about 50° C. In these low temperature application, the means for heating the chemo/electro-active materials may be a voltage source that has a voltage in the range of about $10^{-3}$ to about $10^{-6}$ volts. The substrate on which the materials are placed may be made of a materials that is selected from one or more of the group consisting of silicon, silicon carbide, silicon nitride, and alumina containing a resistive dopant. Devices used in these low temperature applications are often small enough to be held in the human hand.

This heating technique is also applicable, however, to the analysis of high temperature gases. When the temperature of the gas mixture is above about 400° C., the sensor materials may nevertheless be maintained by a heater at a constant or substantially constant preselected temperature that is higher than the temperature of the gas mixture. Such preselected temperature may be about 500° C. or above, about 600° C. or above, about 700° C. or above, about 800° C. or above, about 900° C. or above, or about 1000° C. or above. Should the temperature of the gas mixture exceed the temperature preselected for the heater, the heater may cycle off during such time. A temperature sensor will still be employed, however, to measure the temperature of the sensor materials and provide that value as an input to an algorithm by which information related to the composition of the gas mixture is determined.

What is claimed is:

1. A method for controlling a process that emits a multi-component mixture of gases, wherein the mixture is comprised of various individual component gases each of which has an individual concentration within the mixture; wherein a subgroup of the mixture is comprised of at least two but less than all of the component gases of the mixture; wherein the members of a subgroup of gases together have a collective concentration within the mixture; and wherein the method comprises
    (a) providing at least first and second signals, the first signal being related to the individual concentration within the unseparated components of the emitted gas mixture of an individual component gas therein, and the second signal being related to the collective concentration within the unseparated components of the emitted gas mixture of a subgroup of the component gases therein;
    (b) inputting the signal(s) to a decision-making routine for controlling the process; and
    (c) outputting a signal from the decision-making routine for adjusting an operating characteristic of the process.

2. A method according to claim 1 comprising providing a third signal that is related to the individual concentration within the emitted gas mixture of a second individual component gas therein.

3. A method according to claim 1 comprising providing a third signal that is related to the collective concentration within the emitted gas mixture of a second subgroup of component gases therein.

4. A method according to claim 1 wherein at least one signal is the concentration within the emitted gas mixture of an individual component gas or a subgroup of component gases.

5. A method according to claim 1 wherein at least one signal is related to voltage, current, resistance, impedance, or capacitance.

6. A method according to claim 1 wherein the individual component gas within the gas mixture is selected from the group consisting of oxygen, carbon monoxide, hydrogen, sulfur dioxide, ammonia, $CO_2$, $H_2S$, methanol, and water.

7. A method according to claim 1 wherein the individual component gas within the gas mixture is not oxygen.

8. A method according to claim 1 wherein the components of a subgroup comprise hydrocarbons or nitrogen oxides.

9. A method according to claim 1 wherein the process is a chemical reaction in which reactants are reacted, and the adjusted operating characteristic is the relative amount of the reactants in the reaction.

10. A method according to claim 1 wherein the process is combustion in an internal combustion engine.

11. A method according to claim 10 wherein the signal is provided from an array of chemo/electro-attive materials, and the array is located upstream or downstream from a catalytic converter or a device for the storage or abatement of $NO_x$.

12. A method according to claim 1 wherein the process is a biochemical reaction.

13. A method according to claim 1 wherein (a) the process is a chemical reaction (b) a product of the chemical reaction is transmitted to a device, and (c) the method further comprises situating an operating characteristic of the device.

14. A method according to claim 1 or 13 wherein at least one signal is provided by exposing an array of chemo/electro-active materials to the gas mixture.

15. A method according to claim 14 wherein at least one signal is proportional to the electrical resistance of a chemo/electro-active material when exposed to the gas mixture.

16. A method according to claims 1 or 15 wherein the first and second signals are determined on the occasion of being provided for input into the decision-making routine.

17. A method according to claims 1 or 15 wherein the first and second signals are inputted to a map.

18. A method according to claim 17 wherein the map relates information about the composition of the emitted gas mixture to information about an operating characteristic of the process.

19. A method according to claim 1 or 15 wherein an individual component gas within the gas mixtute is oxygen, and the components of a subgroup comprise hydrocarbons.

20. A method according to claim 1 or 13 wherein an individual component gas within the gas mixture is a reducing agent, and the components of a subgroup comprise nitrogen oxides.

21. A method according to claim 13 wherein the device is an internal combustion engine or a pollution abatement device.

22. A method according to claim 21 wherein the first and second signals are provided from an array of at least four chemo/electro-active materials, and the array is located upstream or downstream from a catalytic converter or a device for the storage or abatement of $NO_x$.

23. A method according to claim 10 or 21 wherein the decision-making routine controls the ratio of air to fuel supplied to the engine, controls an exhaust gas recycle valve for the engine, controls engine speed, or controls a pollution abatement device.

24. A method according to claim 12 wherein the biochemical reaction comprises fermentation.

25. A method according to claim 14 or 22 wherein the array of chemo/electro-active materials comprises at least four chemo/electro-active materials.

26. A method according to claim 14 or 22 wherein the chemo/electro-active materials comprise (a) one or more members of the group consisting of $M^1O_x$, $M^1_aM^2_bO_x$ and $M^1_aM^2_bM^3_cO_x$ wherein $M^1$, $M^2$, $M^3$, a, b, c and x are as set forth below:

$M^1$ is selected from the group consisting of Al, Ce, Cr, Cu, Fe, Ga, Mn, Nb, Ni, Pr, Sb, Sn, Ta, Ti, W and Zn;

$M^2$ and $M^3$ are each independently selected from the group consisting of Ga, La, Mn, Ni, Sn, Sr, Ti, W, Y, Zn;

$M^1$ and $M^2$ ave each different in $M^1_aM^2_bO_x$, and $M^1$, $M^2$ and $M^3$ are each different in $M^1_aM^2_bM^3_cO_x$;

a, b and c are each independently about 0.0005 to about 1; and x is a number sufficient so tat the oxygen present balances the charges of the other elements in the chemo/electro-active material; or (b) one or more members of the group consisting of $Al_aNi_bO_x$, $CeO_2$, $Cr_aMn_bO_x$, $Cr_aTi_bO_x$, $Cr_aY_bO_x$, $Cu_aGa_bO_x$, $Cu_aLa_bO_x$, $CuO$, $Fe_aLa_bO_x$, $Fe_aNi_bO_x$, $Fe_aTi_bO_x$, $Ga_aTi_bZn_cO_x$, $Mn_aTi_bO_x$, $Nb_aSr_bO_x$, $Nb_aTi_bO_x$, $Nb_aTi_bZn_cO_x$, $Nb_aW_bO_x$, $NiO$, $Ni_aZn_bO_x$, $Pr_6O_{11}$, $Sb_aSn_bO_x$, $SnO_2$, $Ta_aTi_bO_x$, $Ti_aZn_bO_x$, $WO_3$ and $ZnO$; wherein a, b, and c are each independently about 0.0005 to about 1; and wherein x is a number sufficient so that the oxygen present balances the charges of the other elements in the chemo/electro-active material.

27. An apparatus for controlling a process that emits a multi-component mixture of gases, wherein the mixture is comprised of various individual component gases each of which has an individual concentration within the mixture; wherein a subgroup of the mixture is comprised of at least two but less than all of the component gases of the mixture; wherein the members of a subgroup of gases together have a collective concentration within the mixture; and wherein the apparatus comprises (a) an array of chemo/electro-active materials;

(b) means for determining the electrical response of each chemo/electro-active material upon exposure of the array to the unseparated components of the emitted gas mixture;

(c) means for determining (i) information related to the individual concentration within the emitted gas mixture of an individual component gas therein, and (ii) information related to the collective concentration within the emitted gas mixture of a subgroup of the component gases therein; and (d) a decision-making routine for controlling the process in view of the information determined about the composition of the emitted gas mixture.

28. An apparatus according to claim 27 wherein (a) the process is a chemical reaction (b) a product of the chemical reaction is transmitted to a device, and (c) the decision-making routine controls the operation of the device.

29. An apparatus according to claim 27 wherein (a) the process is a chemical reaction (b) a product of the chemical reaction is transmitted to a device, and (c) the apparatus further comprises a decision-making routine for controlling the operation of the device in view of the information determined about the composition of the emitted gas mixture.

30. An apparatus according to claim 27, 28 or 29 which comprises means to determine the information about the composition of the emitted gas mixture, to be provided to the decision making routine, on the occasion of providing the information to the decision-making routine.

31. An apparatus according to claim 27, 28 or 29 further comprising a map to which the information about the composition of the emitted gas mixture is inputted.

32. An apparatus according to claim 31 wherein the map relates information about the composition of the emitted gas mutture to information about an operating characteristic of the process.

33. An apparatus according to claim 27 wherein the information about the composition of the gas mixture comprises the individual concentration therein of an individual component gas of the mixture.

34. An apparatus according to claim 27 wherein the information about the composition of the gas mixture comprises the collective concentration within the emitted gas mixture of a subgroup of the component gases therein.

35. An apparatus according to claim 27 wherein an individual component gas within the gas mixture is selected from the group consisting of oxygen, carbon monoxide, hydrogen, sulfur dioxide, ammonia, $CO_2$, $H_2S$, methanol and water.

36. An apparatus according to claim 27 wherein the conponents of a subgroup comprise hydrocarbons or nitrogen oxides.

37. An apparatus according to claim 27, 28 or 29 wherein an individual component gas within the gas mixture is oxygen, and the components of a subgroup comprise hydrocarbons.

38. An apparatus according to claim 27, 28 or 29 wherein an individual component gas within the gas mixture is a reducing agent and the components of a subgroup comprise nitrogen oxides.

39. An apparatus according to claim 27 wherein the process is a chemical reaction in which reactants are reacted, and the decision-making routine adjusts the relative amount of reactants in the reaction.

40. An apparatus according to claim 27 wherein the controlled process is combustion in an internal combustion engine.

41. An apparatus according to claim 28 or 29 wherein the device is an internal combustion engine or a pollution abatement device.

42. An apparatus according to claim 40 wherein the array of chemo/electro-active materials is located upstream or downstream from a catalytic converter or a device for the storage or abatement of $NO_x$.

43. An apparatus according to claim 41 wherein the array of chemo/electro-active materials is located upstream or downstream from a catalytic converter or a device for the storage or abatement of $NO_x$.

44. An apparatus according to claim 40 wherein the decision-making routine controls the ratio of air to fuel supplied to the engine, or controls an exhaust gas recycle valve for the engine, controls engine speed, or controls a pollution abatement device.

45. An apparatus according to claim 27 wherein the process or reaction is a biochemical reaction.

46. An apparatus according to claim 45 wherein the biochemical reaction is fermentation.

47. An apparatus according to claim 27, 28 or 29 wherein the array of chemo/electro-active materials comprises at least four chemo/electro-active materials.

48. A method according to claim 27, 28 or 29 wherein the chemo/electro-active materials comprise (a) one or more members of the group consisting of $M^1O_x$, $M^1_aM^2_bO_x$ and $M^1_aM^2_bM^3_cO_x$ wherein $M^1$, $M^2$, $M^3$, a, b, c and x are as set forth below:

$M^1$ is selected from the group consisting of Al, Ce, Cr, Cu, Fe, Ga, Mn, Nb, Ni, Pr, Sb, Sn, Ta, Ti, W and Zn;

$M^2$ and $M^3$ are each independently selected from the group consisting of Ga, La, Mn, Ni, Sn, Sr, Ti, W, Y, Zn;

$M^1$ and $M^2$ are each different in $M^1_aM^2_bO_x$, and $M^1$, $M^2$ and $M^3$ are each different in $M^1_aM^2_bM^3_cO_x$;

a, b and c are each independently about 0.0005 to about 1; and x is a number sufficient so that the oxygen present balances the charges of the other elements in the chemo/electro-active material; or (b) one or more members of the group consisting of $Al_aNi_bO_x$, $CeO_2$, $Cr_aMn_bO_x$, $Cr_aTi_bO_x$, $Cr_aY_bO_x$, $Cu_aGa_bO_x$, $Cu_aLa_bO_x$, $CuO$, $Fe_aLa_bO_x$, $Fe_aNi_bO_x$, $Fe_aTi_bO_x$, $Ga_aTi_bZn_cO_x$, $Mn_aTi_bO_x$, $Nb_aSr_bO_x$, $Nb_aTi_bO_x$, $Nb_aTi_bZn_cO_x$, $Nb_aW_bO_x$, $NiO$, $Ni_aZn_bO_x$, $Pr_6O_{11}$, $Sb_aSn_bO_x$, $SnO_2$, $Ta_aTi_bO_x$, $Ti_aZn_bO_x$, $WO_3$ and ZnO; wherein a, b, and c are each independently about 0.0005 to about 1; and wherein x is a number sufficient so that the oxygen present balances the charges of the other elements in the chemo/electro-active material.

49. An apparatus according to claim 27, 28 or 29 which is a component part of a vehicle for transportation or a piece of equipment for construction, maintenance or industrial operations.

\* \* \* \* \*